United States Patent
Li et al.

(10) Patent No.: US 8,680,097 B2
(45) Date of Patent: Mar. 25, 2014

(54) BENZOTHIOPHENE ALKANOL PIPERAZINE DERIVATIVES AND THEIR USE AS ANTIDEPRESSANT

(75) Inventors: Jianqi Li, Shanghai (CN); Kai Gao, Shanghai (CN); Na Lv, Shanghai (CN)

(73) Assignees: CSPC Zhongqi Pharmaceutical Technology (Shijiazhuang) Co. Ltd. (CN); Shanghai Institute of Pharmaceutical Industry (CN)

( * ) Notice: Subject to any disclaimer, the term of this patent is extended or adjusted under 35 U.S.C. 154(b) by 190 days.

(21) Appl. No.: 13/001,998

(22) PCT Filed: Jun. 30, 2009

(86) PCT No.: PCT/CN2009/072534
§ 371 (c)(1),
(2), (4) Date: Dec. 29, 2010

(87) PCT Pub. No.: WO2010/000198
PCT Pub. Date: Jan. 7, 2010

(65) Prior Publication Data
US 2011/0118263 A1  May 19, 2011

(30) Foreign Application Priority Data
Jul. 2, 2008  (CN) .......................... 2008 1 0040105

(51) Int. Cl.
| A61K 31/496 | (2006.01) |
| A61K 31/5377 | (2006.01) |
| C07D 333/58 | (2006.01) |
| C07D 409/12 | (2006.01) |
| C07D 413/12 | (2006.01) |

(52) U.S. Cl.
USPC .............. 514/233.5; 514/252.13; 514/252.14; 514/253.11; 544/121; 544/295; 544/364; 544/376

(58) Field of Classification Search
None
See application file for complete search history.

(56) References Cited

U.S. PATENT DOCUMENTS

| 7,276,603 B2 | 10/2007 | Venkatesan et al. |
| 7,576,086 B2 | 8/2009 | Li et al. |
| 2005/0267121 A1 | 12/2005 | Li et al. |

FOREIGN PATENT DOCUMENTS

| CN | 1384102 A | 12/2002 |
| CN | 1812984 A | 8/2006 |
| CN | 1844120 A | 10/2006 |
| CN | 1935807 A | 3/2007 |
| CN | 1948297 A | 4/2007 |
| EP | 1008594 A1 | 6/2000 |
| WO | WO-0244170 A2 | 6/2002 |

OTHER PUBLICATIONS

"International Application Serial No. PCT/CN2009/072534, International Preliminary Report on Patentability completed Sep. 30, 2010", (w/English Translation), 17 pgs.
"International Application Serial No. PCT/CN2009/072534, Written Opinion mailed Oct. 15, 2009", (w/ English Translation), 10 pgs.
Saulter, F., et al., "N-Substituted 2-methyl-3-aminoacetyl-benzol[b]thiothene and 2-methyl-3-(α-hydroxyl-β-aminoethyl)benzol[b]thiophen.", (Abstract No. 12797g), Chemical Abstracts, 68(3), (Jan. 15, 1968), pg. 1219.
"International Application Serial No. PCT/CN2009/072534,International Search Report mailed Oct. 15, 2009", 7 pgs.
Sauter, F., et al., "N-Substituierte 2-Methyl-3-aminoacetyl-benzol[b]thiothene und 2-Methyl-3-(αhydroxyl-β-amino-äthyl)-benzo[b]thiophene", Monatsh. Chem., 98(5), (w/ English Abstract), (1967), 6 pgs.
"European Application Serial No. 09771968.6, Supplementary European Search Report mailed Oct. 25, 2011", 6 pgs.

*Primary Examiner* — Emily Bernhardt
(74) *Attorney, Agent, or Firm* — Scwegman Lundberg & Woessner, P.A.

(57) ABSTRACT

The invention discloses benzothiophene alkanol piperazine derivatives and their use as antidepressants. The invention discloses the said benzothiophene alkanol piperazine derivative having triple inhibition effect on the reuptake of 5-HT, NA and DA. Compared with clinical used antidepressants so far having single target, e.g. desipramine and fluoxetine, and clinical used antidepressants so far having double targets, e.g venlafaxine and duloxetine, the said benzothiophene alkanol piperazine derivatives of the present invention may have a broader indication range and less toxic and side effects to nervous system. The benzothiophene alkanol piperazine derivatives are the compounds with the following formula or their pharmaceutically acceptable salts, wherein $Ar_1$, $R_1$-$R_4$, X, Y, m and n have the same definition as defined in claim 1.

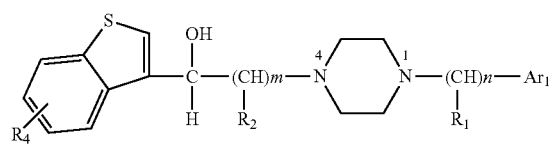

7 Claims, No Drawings

BENZOTHIOPHENE ALKANOL PIPERAZINE DERIVATIVES AND THEIR USE AS ANTIDEPRESSANT

RELATED APPLICATIONS

This application is the national stage application under 35 U.S.C. 371 of PCT/CN2009/072534, filed Jun. 30, 2009 and published as WO 2010/000198 A1 on Jan. 7, 2010, which claimed priority under 35 U.S.C. 119 to Chinese Patent Application No. 200810040105.4, filed Jul. 2, 2008; which applications and publication are incorporated herein by reference in their entirety.

FIELD OF INVENTION

The present invention relates to benzothiophene alkanol piperazine derivatives and their use as broad-spectrum antidepressants.

BACKGROUND OF THE INVENTION

Depression is a syndrome characterized by significant and lasting low mood, which mainly manifests as affective disorder. The symptoms include low mood, less speech, slow mentality and motion, and even suicide attempt.

Depression, as a chronic mental disease, has become a major problem which bothers the medical health service in China, due to long treatment course, slow effect onset and higher rate of relapse, disability and suicide. According to "World Health Reports" announced by World Health Organization (WHO), depression has become the fourth largest disease in the world, and depression might become the second largest illness after heart disease by 2020, and thus become a serious problem to human health.

By now, the action mechanism of antidepressant has not been clearly demonstrated. Drugs having definite effect substantially act on synapses of the nerve ending, and exert their curative effects by adjusting the level of neurotransmitters in synaptic cleft. The biochemistry study on etiology indicated that depression relates mainly to five types of neurotransmitters, i.e., central 5-hydroxytryptamine (5-HT), noradrenaline (NA), dopamine (DA), acetylcholine (Ach), and γ-aminobutyric acid (GABA).

Antidepressant can be divided into two categories: early non-selective antidepressants and novel selective reuptake inhibitors. Non-selective antidepressants mainly include monoamine oxidase inhibitors (MAOIs) and tricyclic antidepressants (TCAs); selective reuptake inhibitors mainly comprise selective 5-hydroxytryptamine (5-HT) reuptake inhibitors (SSRIs), noradrenaline (NA) reuptake inhibitors (NRIs), noradrenergic and specific 5-HT reuptake inhibitors (NDRIs), 5-HT and NA reuptake inhibitors (SNRIs), 5-HT re-absorption enhancers, and the like.

There are two trends in the worldwide situation of studies on antidepressant:

One is redevelopment of existing drugs. It includes: 1) further development of new indications of existing drugs, and 2) change of dosage forms of existing drugs.

Another is further development of new products, i.e., develop novel antidepressants with better antidepressant effects, faster onset of action and higher safety than existing commercial available drugs by seeking new structural type of compound which acts on a new target or multiple action targets.

Chinese patent application No. 2006100135485 disclosed a benzo[b]thiophene compound modified with substituted phenylpiperazine for the treatment of depression. However, it is hard to be practically applied since no pharmacological data of anti-depression effect in vitro and in vivo was available.

Up to date, existing antidepressants still cannot meet the treatment demand. Research on triple selective reuptake inhibitors is continuously drawing attention, and is expected to solve the hysteresis effect of existing antidepressants, and to improve effectiveness and increase safety etc. Triple selective reuptake inhibitors, also known as "broad spectrum" antidepressants, are compounds which are able to simultaneously selectively inhibit three types of monoamine transmitters 5-HT, NA and DA closely related to depression.

Studies on 5-HT, NA and DA triple selective reuptake inhibitors developed based on dual reuptake inhibitors have become focus of current antidepressants research, which will have more advantages in onset of action and effectiveness.

Novel triple selective reuptake inhibitors are now still on clinical research stage. For example, triple selective reuptake inhibitor DOV-216303 developed by DOV Pharmaceutical Inc. is on phase III clinical trial; NS-2359 jointly developed by GlaxoSmithKline and NeuroSearch Inc. is on phase II antidepressant clinical trial now. These monoamine transmitter triple selective reuptake inhibitors possess advantages in high effectiveness and fast onset of action and are becoming hot points in the antidepressants field. Research and development of antidepressants is still at its preliminary stage, especially for the research on novel triple routing antidepressants acting on 5-HT, NA and DA, which will further attract increasing attention.

DESCRIPTION OF THE INVENTION

One of the objects of the present invention is to provide a type of benzothiophene alkanol piperazine derivative, to overcome the defects of existing antidepressants in prior art, i.e., slow onset, low efficacy, side effects and poor safety etc., and thus meet the requirements of treating depression.

Another object of the present invention is to provide the use of above mentioned derivative as novel antidepressants.

The benzothiophene alkanol piperazine derivative mentioned in the present invention is a compound of formula (1)

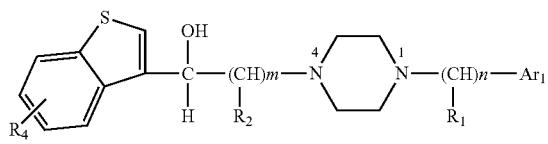

(1)

or a pharmaceutically acceptable salt thereof, wherein the pharmaceutically acceptable salt thereof is a hydrochloride salt, a hydrobromide salt, a sulphate salt, a trifluoro acetate salt or a methanesulfonate salt, preferred pharmaceutically acceptable salt is a hydrochloride salt, a hydrobromide salt, and the pharmaceutically acceptable salt may contain 0.5 to 3 molecules of crystal water;

wherein,

Ar$_1$ represents:

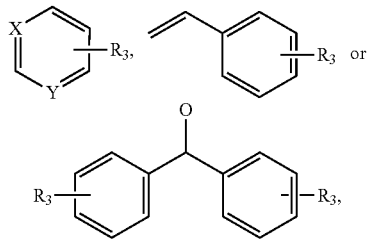

R$_1$ and R$_2$ each independently represents hydrogen; C$_1$-C$_6$ alkyl; C$_5$ or C$_6$ alicyclic ring; phenyl; or phenyl substituted by C$_1$-C$_6$ alkyl, C$_1$-C$_6$ alkoxy or halo groups;

R$_3$ and R$_4$ each independently represents hydrogen; C$_1$-C$_6$ alkyl, phenyl; or phenyl substituted by one to four substituents independently selected from the group consisting of C$_1$-C$_6$ alkyl, C$_1$-C$_6$ alkoxy, hydroxyl, amino or halo; a 5-member or 6-member ring containing N or O; hydroxyl; C$_1$-C$_6$ alkoxy; amino; amino substituted by C$_1$-C$_6$ alkyl or C$_1$-C$_6$ haloalkyl; halo; carboxylic acid; carboxylic acid ester; nitro or acetonitrile;

X represents C or N;
Y represents C or N;
m is 1, 2 or 3, and
n is 1, 2 or 3.

Preferred R$_3$ is hydrogen; C$_1$-C$_2$ alkyl; hydroxyl; methoxy; ethoxy; amino; amino substituted by C$_1$-C$_6$ alkyl or C$_1$-C$_6$ haloalkyl; fluorine atom; phenyl; or phenyl substituted by one to four substituents independently selected from the groups consisting of C$_1$-C$_6$ alkyl, C$_1$-C$_6$ alkoxy, hydroxyl, amino and halo; more preferred R$_3$ is C$_1$-C$_2$ alkyl or fluorine atom.

Asymmetric carbons in the structure of the compound are achiral carbon atoms or chiral carbon atoms with R or S configuration.

Preferred compound include:
VII-1  N$^1$-benzyl-N$^4$-[2-hydroxy-2-(benzo[b]thiophene-3-yl)]ethylpiperazine,
VII-2  N$^1$-benzhydryl-N$^4$-[2-hydroxy-2-(benzo[b]thiophene-3-yl)]ethylpiperazine,
VII-3  N$^1$-(p-chlorobenzyl)-N$^4$-[2-hydroxy-2-(benzo[b]thiophene-3-yl)]ethylpiperazine,
VII-4  N$^1$-benzyl-N$^4$-[1-methyl-2-hydroxy-2-(benzo[b]thiophene-3-yl)]ethylpiperazine (threo isomer),
VII-5  N$^1$-benzyl-N$^4$-[1-methyl-2-hydroxy-2-(benzo[b]thiophene-3-yl)]ethylpiperazine (erythro isomer),
VII-6  N$^1$-p-aminobenzyl-N$^4$-[1-methyl-2-hydroxy-2-(benzo[b]thiophene-3-yl)]ethylpiperazine,
VII-7  N$^1$-p-methoxybenzyl-N$^4$-[1-methyl-2-hydroxy-2-(benzo[b]thiophene-3-yl)]ethylpiperazine,
VII-8  N$^1$-p-ethoxybenzyl-N$^4$-[1-methyl-2-hydroxy-2-(benzo[b]thiophene-3-yl)]ethylpiperazine,
VII-9  N$^1$-(p-hydroxybenzyl-N$^4$-[1-methyl-2-hydroxy-(benzo[b]thiophene-3-yl)]ethylpiperazine,
VII-10  N$^1$-benzyl-N$^4$-[3-hydroxy-3-(benzo[b]thiophene-3-yl)]propylpiperazine,
VII-11  N$^1$-cinnamyl-N$^4$-[3-hydroxy-3-(benzo[b]thiophene-3-yl)]propylpiperazine,
VII-12  N$^1$-α-phenethyl -N$^4$-[3-hydroxy-3-(benzo[b]thiophene-3-yl)]propylpiperazine,
VII-13  N$^1$-p-methoxylbenzyl)-N$^4$-[3-hydroxy-3-(benzo[b]thiophene-3-yl)]propylpiperazine,
VII-14  N$^1$-benzhydryl-N$^4$-[3-hydroxy-3-(benzo[b]thiophene-3-yl)]propylpiperazine,
VII-15  N$^1$-(4,4'-difluorodiphenylmethoxypethyl-N$^4$-[3-hydroxy-3-(benzo[b]thiophene-3-yl))propylpiperazine,
VII-16  N$^1$-benzyl-N$^4$-[2-methyl-3-hydroxy-3-(benzo[b]thiophene-3-yl)]propylpiperazine,
VII-17  N$^1$-cinnamyl-N$^4$-[2-methyl-3-hydroxy-3-(benzo[b]thiophene-3-yl)]propylpiperazine,
VII-18  N$^1$-benzhydryl-N$^4$-[2-methyl-3-hydroxy-3-(benzo[b]thiophene-3-yl)]propylpiperazine,
VII-19  N$^1$-(4,4'-difluorodiphenylmethoxy)ethyl-N$^4$-[2-methyl-3-hydroxy-3-(benzo[b]thiophene-3-yl)]propylpiperazine,
VII-20  N$^1$-benzyl-N$^4$-[2-butyl-3-hydroxy-3-(benzo[b]thiophene-3-yl)]propylpiperazine,
VII-21  N$^1$-α-phenethyl-N$^4$-[2-butyl-3-hydroxy-3-(benzo[b]thiophene-3-yl)]propylpiperazine,
VII-22  N$^1$-(p-chlorobenzyl)-N$^4$-[2-butyl-3-hydroxy-3-(benzo[b]thiophene-3-yl)]propylpiperazine,
VII-23  N$^1$-(p-methoxybenzyl)-N$^4$-[2-butyl-3-hydroxy-3-(benzo[b]thiophene-3-yl)]propylpiperazine,
VII-24  N$^1$-benzyl-N$^4$-[4-hydroxy-4-(benzo[b]thiophene-3-yl)]butylpiperazine,
VII-25  N$^1$-α-phenethyl-N$^4$-[4-hydroxy-4-(benzo[b]thiophene-3-yl)]butylpiperazine,
VII-26  N$^1$-p-nitrobenzyl-N$^4$-[4-hydroxy-4-(benzo[b]thiophene-3-yl)]butylpiperazine,
VII-27  N$^1$-p-aminobenzyl-N$^4$-[4-hydroxy-4-(benzo[b]thiophene-3-yl)]butylpiperazine,
VII-28  N$^1$-cinnamyl-N$^4$-[4-hydroxy-4-(benzo[b]thiophene-3-yl)]butylpiperazine,
VII-29  N$^1$-benzhydryl-N$^4$-[4-hydroxy-4-(benzo[b]thiophene-3-yl)]butylpiperazine,
VII-30  N$^1$-(4,4'-difluorodiphenylmethoxy)ethyl-N$^4$-[4-hydroxy-4-(benzo[b]thiophene-3-yl)]butylpiperazine,
VII-31  N$^1$-(p-methoxylcinnamyl)-N$^4$-[3-hydroxy-3-(benzo[b]thiophene-3-yl)]propylpiperazine,
VII-32  N$^1$-p-aminocinnamyl-N$^4$-[3-hydroxy-3-(benzo[b]thiophene-3-yl)]propylpiperazine,
VII-33  N$^1$-(4,4-difluorodiphenylmethoxy)ethyl-N$^4$-[3-hydroxy-3-(benzo[b]thiophene-3-yl)]propylpiperazine,
VII-34  N$^1$-(4,4-dihydroxydiphenylmethoxy)ethyl-N$^4$-[3-hydroxy-3-(benzo[b]thiophene-3-yl)]propylpiperazine,
VII-35  N$^1$-p-nitrocinnamyl-N$^4$-[3-hydroxy-3-(benzo[b]thiophene-3-yl)]propylpiperazine,
VII-36  N$^1$-benzyl-N$^4$-[3-hydroxy-3-(5-methylbenzo[b]thiophene-3-yl)]propylpiperazine,
VII-37  N$^1$-benzyl-N$^4$-[3-hydroxy-3-(5-methoxylbenzo[b]thiophene-3-yl)]propylpiperazine,
VII-38  N$^1$-benzyl-N$^4$-[3-hydroxy-3-(6-aminobenzo[b]thiophene-3-yl)]propylpiperazine,
VII-39  N$^1$-benzyl-N$^4$-[3-hydroxy-3-(6-chlorobenzo[b]thiophene-3-yl)]propylpiperazine,
VII-40  N$^1$-benzyl-N$^4$-[3-hydroxy-3-(6-methylaminobenzo[b]thiophene-3-yl)]propylpiperazine,
VII-41  N$^1$-(β-pyridinemethyl)-N$^4$-[2-methyl-3-hydroxy-3-(benzo[b]thiophene-3-yl)]propylpiperazine,
VII-42  N$^1$-(4-morpholinebenzyl)-N$^4$-[2-methyl-3-hydroxy-3-(benzo[b]thiophene-3-yl)]propylpiperazine, and
VII-43  N$^1$-benzyl-N$^4$-[2-cyclopentylmethyl-3-hydroxy-3-(benzo[b]thiophene-3-yl)]propylpiperazine.

Most preferred benzothiophene alkanol piperazine derivative is VII-10, i.e, N$^1$-benzyl-N$^4$-[3-hydroxy-3-(benzo[b]thiophene-3-yl)propylpiperazine.

The structures are shown in Table 1.

TABLE 1

| No. | Ar₁ | R₁ | R₂ | R₄ | X | Y | n | m |
|---|---|---|---|---|---|---|---|---|
| VII-1 | Ph | H | H | H | C | C | 1 | 1 |
| VII-2 | Ph | Ph | H | H | C | C | 1 | 1 |
| VII-3 | 4-Cl-C₆H₄ | H | H | H | C | C | 1 | 1 |
| VII-4 | Ph | H | CH₃ | H | C | C | 1 | 1 |
| VII-5 | Ph | H | CH₃ | H | C | C | 1 | 1 |
| VII-6 | 4-NH₂-C₆H₄ | H | CH₃ | H | C | C | 1 | 1 |
| VII-7 | 4-OCH₃-C₆H₄ | H | CH₃ | H | C | C | 1 | 1 |
| VII-8 | 4-OCH₂CH₃-C₆H₄ | H | CH₃ | H | C | C | 1 | 1 |
| VII-9 | 4-OH-C₆H₄ | H | CH₃ | H | C | C | 1 | 1 |
| VII-10 | Ph | H | H | H | C | C | 1 | 2 |
| VII-11 | Ph | H | H | H | C | C | 1 | 2 |
| VII-12 | Ph | CH₃ | H | H | C | C | 1 | 2 |
| VII-13 | 4-CH₃-C₆H₄ (OCH₃) | H | H | H | C | C | 1 | 2 |
| VII-14 | Ph | Ph | H | H | C | C | 1 | 2 |
| VII-15 | (4-F-C₆H₄)₂CH-O- | H | H | H | C | C | 2 | 2 |
| VII-16 | Ph | H | CH₃ | H | C | C | 1 | 2 |
| VII-17 | CH₂=CH-C₆H₄ | H | CH₃ | H | C | C | 1 | 2 |
| VII-18 | Ph | Ph | CH₃ | H | C | C | 1 | 2 |
| VII-19 | (4-F-C₆H₄)₂CH-O- | H | CH₃ | H | C | C | 2 | 2 |

TABLE 1-continued

| No. | Ar₁ | R₁ | R₂ | R₄ | X | Y | n | m |
|---|---|---|---|---|---|---|---|---|
| VII-20 | Ph | H | C₄H₉ | H | C | C | 1 | 1 |
| VII-21 | Ph | CH₃ | C₄H₉ | H | C | C | 1 | 2 |
| VII-22 | 4-Cl-C₆H₄ | H | C₄H₉ | H | C | C | 1 | 2 |
| VII-23 | 4-OCH₃-C₆H₄ | H | C₄H₉ | H | C | C | 1 | 2 |
| VII-24 | Ph | H | H | H | C | C | 1 | 3 |
| VII-25 | Ph | CH₃ | H | H | C | C | 1 | 3 |
| VII-26 | 4-NO₂-C₆H₄ | H | H | H | C | C | 1 | 3 |
| VII-27 | 4-NH₂-C₆H₄ | H | H | H | C | C | 1 | 3 |
| VII-28 | CH₂=CH-C₆H₅ | H | H | H | C | C | 1 | 3 |
| VII-29 | Ph | Ph | H | H | C | C | 1 | 3 |
| VII-30 | (4-F-C₆H₄)₂CH-O- | H | H | H | C | C | 2 | 3 |
| VII-31 | 4-OCH₃-C₆H₄-CH=CH₂ | H | H | H | C | C | 1 | 2 |
| VII-32 | 4-NH₂-C₆H₄-CH=CH₂ | H | H | H | C | C | 1 | 2 |
| VII-33 | (4-Cl-C₆H₄)₂CH-O- | H | H | H | C | C | 1 | 2 |
| VII-34 | (4-HO-C₆H₄)₂CH-O- | H | H | H | C | C | 1 | 2 |

TABLE 1-continued
| No. | Ar₁ | R₁ | R₂ | R₄ | X | Y | n | m |
|---|---|---|---|---|---|---|---|---|
| VII-35 | 4-NO₂-styryl-phenyl | H | H | H | C | C | 1 | 2 |
| VII-36 | Ph | H | H | CH₃ | C | C | 1 | 2 |
| VII-37 | Ph | H | H | OCH₃ | C | C | 1 | 2 |
| VII-38 | Ph | H | H | NH₂ | C | C | 1 | 2 |
| VII-39 | Ph | H | H | Cl | C | C | 1 | 2 |
| VII-40 | Ph | H | H | NHCH₃ | C | C | 1 | 2 |
| VII-41 | 3-methylpyridin-yl | H | CH₃ | H | N | C | 1 | 2 |
| VII-42 | 4-morpholino-methylphenyl | H | CH₃ | H | C | C | 1 | 2 |
| VII-43 | Ph | H | cyclopentyl | H | C | C | 1 | 2 |
The compounds of the present invention can be synthesized by the following method:
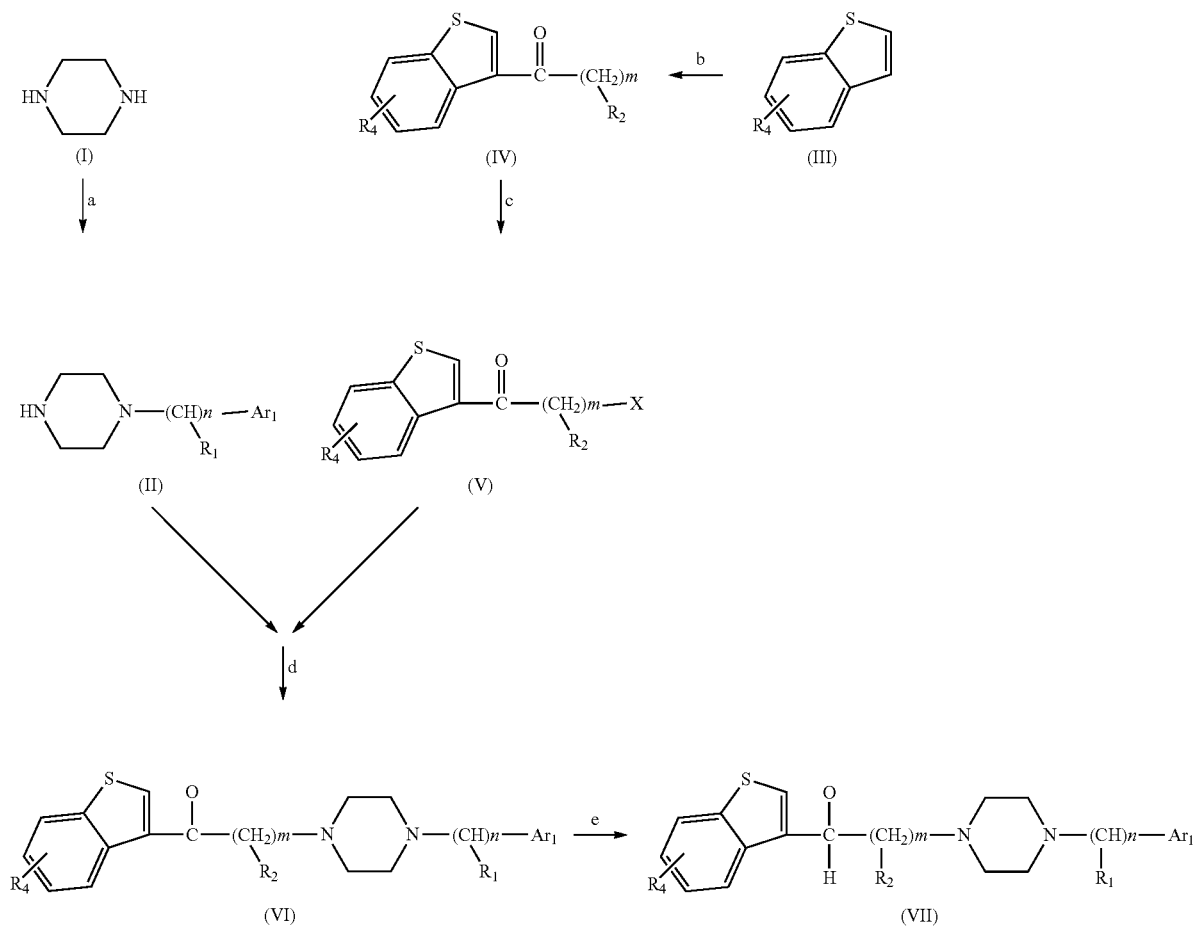

During the above process:

a:

b:
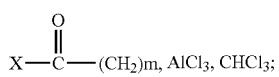

c:

d:

e:

The synthesis of said benzothiophene alkanol piperazine derivatives is started from piperazine (I). Firstly a nucleophilic substitution reaction with a corresponding halogenated arylalkane is performed to obtain N-monoalkylated compound (II). This reaction is carried out in phase transfer catalytic condition, using cetyltrimethylammonium bromide (CTAB) as the phase transfer catalyst, and in a reaction media of benzene/water. N-monoalkylation of piperazine may be carried out under the action of KOH, and the yield may be up to 86%.

Compound (III) is reacted with corresponding acid chloride to carry out a Friedel-Crafts reaction to obtain benzothiophene alkanone (IV). This reaction is performed in a solvent of chloroform at room temperature, using anhydrous aluminum chloride as catalyst, and the yield is about 60%.

Compound (IV) is bromized to give halogenated benzothiophene alkanone (V). This reaction is performed under heating to reflux by using $CuBr_2$ as brominating agent and a mixed solution of chloroform and ethyl acetate as solvent, and the yield is about 75%.

Compound (II) can be reacted with compound (V) to conduct $N^4$-alkylation reaction to give benzothiophene alkanone piperazine compound (VI). The reaction is performed under refluxing for 8-24 hours using $K_2CO_3/CH_3COCH_3$ as reaction system to give a yield of 80%. Using the above steps, main intermediate (VI) for preparing target compound (VII) can be obtained.

Compound (VI) is reacted with $NaBH_4$ in methanol at room temperature for 0.5-2 hours to reduce carbonyl group to obtain corresponding benzothiophene alkanol piperazine compounds (VII). Using the above steps, target compounds VII-1 to VII-43 can be obtained.

Haloarylalkane, benzothiophene and substituted benzothiophene compounds (III) and alkyl acid chloride compounds in a, b and c are commercial available, the alkyl acid chloride can also be obtained from corresponding alkanoic acid and sulfoxide chloride by conventional synthetic method.

Said benzothiophene alkanol piperazine derivatives have triple inhibition effect on the reuptake of 5-HT, NA and DA, and can be used to prepare antidepressants.

The benzothiophene alkanol piperazine derivatives in the present invention may be administrated to patients in need thereof in the form of composition by route of oral administration, injection and the like.

Said composition includes therapeutically effective amount of said benzothiophene alkanol piperazine derivatives and their pharmaceutical carrier.

Said carrier is referred to conventional carrier in pharmaceutical field, for example diluents, excipients such as water; adhesive such as cellulose derivatives, gelatin, polyvinylpyrrolidone; fillers such as starch and the like; disintegrating agent such as calcium carbonate, sodium bicarbonate; in addition, other adjuvants such as flavoring agent and sweeteners may be added into the composition.

For oral administration, it may be formulated into conventional solid preparations such as tablet, powder or capsule; for injection administration, it may be formulated into an injection solution.

Various preparations of the composition according to the present invention can be prepared using conventional methods in medicine field, wherein the content of active ingredient is 0.1% to 99.5% (by weight).

The amount administrated in the present invention may vary according to route of administration age and weight of the patient, type and severity of the disease being treated, and the like, and the daily dose is 5-30 mg/kg body weight (oral) or 1-10 mg/kg body weight (injection). The derivatives of the present invention showed antagonism against depression in animal experiments.

The inventor discovered that the structures of the compounds of the present invention are characterized in that $N^1$ position of piperazine is connected to a phenyl ring via 1-3 carbon atoms, the structure of which not only differs from the structural types of the compounds reported in the above patent publications, but also has triple inhibition effect on the reuptake of 5-HT, NA, DA and antidepressant activity in vivo. Compared with clinically used antidepressants so far having single or dual action mechanism, e.g. desipramine, fluoxetine, venlafaxine and the like, the said benzothiophene alkanol piperazine derivatives of the present invention may have a broader indication range, faster onset of effect and less toxic and side effects.

Specific Models for Carrying Out the Invention

General Method 1: synthesis of N-aralkylpiperazine (II) hydrochloride

To 18 ml water, piperazine hexahydrate (350 mmol, from Shanghai chemical reagent station), solid KOH (100 mmol) and CTAB (Hexadecyl Trimethylammonium Bromide, 1 mmol) were added, heated to dissolve 140 ml solution of aralkyl chloride (100 mmol, commercial available) in benzene was added dropwise at the temperature of 70° C. After dropping the reactant was refluxed for 3 hours, allowed to stand, and the organic phase was washed with 50 ml water and 50 ml saturated NaCl solution respectively, dried with $MgSO_4$ and filtered. The solvent was evaporated to dryness under vacuum, and the concentrate was then dissolved in 50 ml absolute alcohol and adjusted to pH of 3 by dropping the solution of $HCl/C_2H_5OH$. Then a solid precipitated and was filtered and dried. N-aralkyl piperazine hydrochloride was obtained by recrystallization with ethanol. The yield was 75-86%.

General Method 2: synthesis of benzothiophene alkanone(IV)

The alkanoyl chloride compound (28.4 mmol) in synthetic route b was dissolved in chloroform (30 ml), and $AlCl_3$ (30.8 mmol) was added. The reactant was stirred for 1 h at room temperature, $AlCl_3$ dissolved gradually, and the color of the solution became darker to light brown. The temperature was controlled below 10° C. To the mixture 10 ml solution of benzothiophene (23.7 mmol) in chloroform was added gradually dropwise. After dropping, the reactant was warmed naturally to room temperature and stirred for 1 h. The color of the reaction solution became darker to brown. The reaction solution was poured into a mixture of hydrochloric acid (20 ml)/crashed ice(50 g) under stirring, and the color of organic phase turned lighter to be light yellow to yellow. The organic phase was separated, washed with water (20 ml×3) till the aqueous phase to be neutral and dried with anhydrous $Na_2SO_4$ overnight. The desiccant was filtered, the residue was washed with small amount of chloroform. Then the solvent of the filtrate was evaporated, and light yellow oily substance was obtained. Light yellow oily product was separated by column chromatography (ethyl acetate: petroleum ether=1: 400~1:60), allowed to stand and solidified. The yield was 75-85%.

General Method 3: synthesis of bromobenzothiophene alkanone(V)

The benzothiophene alkanone (21 mmol) was dissolved in ethyl acetate(50 ml) and chloroform(50 ml), then $CuBr_2$(40.2 mmol) was added, the reaction was performed under refluxing for 3 hours. CuBr produced was filtered out. The filtrate was washed with water (20 ml×3), dried with anhydrous $Na_2SO_4$ overnight. The desiccant was filtered, the residue was washed with a small amount of ethyl acetate. The solvent of the filtrate was evaporated. Light yellow crystalline solid was obtained by recrystallization with ethanol. The yield was about 75%.

General Method 4: synthesis of $N^1$-aralkyl-$N^4$-benzothiophene formyl alkyl piperazine(VI) hydrochloride N-aralkyl piperazine(II) hydrochloride(10 mmol), bromobenzothiophene alkanone (V) (12 mmol), potassium iodide (1 mmol) and anhydrous $K_2CO_3$(35mmol) were placed into acetone (50 ml) to react under stirring at 50° C. for 8 h. After filtered, the solvent was evaporated to dryness under vacuum. 50 ml of water was added, the reactant was extracted with EtOAc (100 ml×3). The ester layers were pooled and washed with 20 ml water and 30 ml saturated NaCl solution successively, dried with $MgSO_4$. After filtration, the solvent was evaporated. The concentrate was dissolved by adding 30 ml of ethanol, and adjusted to a pH of 2 with $HCl/C_2H_5OH$ (5N). The precipitated solid was filtered and recrystallized in ethanol/water or methanol to give a hydrochloride salt of compound (VI).

General Method 5: synthesis of $N^1$-aralkyl-$N^4$-benzothiophene alkanol piperazine (VII) hydrochloride $N^1$-aralkyl-$N^4$-benzothiophene formyl alkyl piperazine hydrochloride (VI) (3.5 mmol) was placed into 60 ml of methanol, and $NaBH_4$ (14 mmol) was added in portions. The reactant was stirred for 1 h at the room temperature. After removing methanol by vacuum evaporation, 20 ml of water was added and the reaction was extracted with EtOAc (40 ml×3). The ester layers were pooled and washed with 20 ml of saturated NaCl solution, then dried with $MgSO_4$. After filtration and the solvent was removed by vacuum evaporation, the residue was dissolved in 20 ml ethanol, and adjusted to a pH of 2 with $HCl/C_2H_5OH$. A solid was precipitated and filtered. The hydrochloride salt of product (VII) was obtained by recrystallization with ethanol/water. If the product was a mixture of threo-form and erythro-form isomer, the corresponding threo-form and erythro-form of the compounds could be obtained by separation through neutral alumina column.

EXAMPLE 1

VII-1 $N^1$-benzyl-$N^4$-[2-hydroxy-2-(benzo[b]thiophene-3-yl)]ethylpiperazine hydrochloride 4.2 g of $N^1$-phenyl-$N^4$-[2-carbonyl-2-(benzo[b]thiophene-3-yl)]ethylpiperazine hydrochloride (12 mmol) was synthesized using $N^1$-benzylpiperazine (20 mmol) and 3-(2-chloracetyl)-benzo[b]thiophene(20 mmol) according to general method 4, then the reduction of carbonyl was performed according to general method 5. 3.2 g of product was obtained in a yield of 75.7%. m.p=267.8-269.4° C.(dec).

MS(m/z): 353.2[M+1]$^+$.

$^1$HNMR(DMSO): 7.81(d, J=7.6 Hz, 1H, Ar—H), 7.70(dd, J=1.6, 6.8 Hz, 1H, Ar—H), 7.28-7.32(m, 4H, Ar—H), 7.24-7.28(m, 3H, Ar—H), 7.22(s, 1H, thiophene), 4.60(d, J=10 Hz, 1H, >CH—OH), 3.54(m, 2H, —CH$_2$-Ph), 2.75-2.78(m, 2H, CH$_2$), 2.52-2.74(m, 8H, piperazine).

EXAMPLE 2

VII-2 $N^1$-benzhydryl-$N^4$-[2-hydroxy-2-(benzo[b]thiophene-3-yl)]ethylpiperazine hydrochloride 3.8 g of $N^1$-benzhydryl-$N^4$-[2-carbonyl-2-(benzo[b]thiophene-3-yl)]ethylpiperazine hydrochloride (9 mmol) was synthesized using $N^1$-benzhydrylpiperazine (20 mmol) and 3-(2-chloracetyl)-benzo[b]thiophene(20 mmol) according to general method 4, then the reduction of carbonyl was performed according to general method 5. 3.1 g of product was obtained in a yield of 80.5%. m.p=278.0-279.8° C.(dec).

MS(m/z): 429.1[M+1]$^+$.

$^1$HNMR(DMSO): 7.78-7.87(m, 4H, Ar—H), 7.28-7.45(m, 10H, Ar—H), 7.22(s, 1H, thiophene), 4.60(d, J=10 Hz, 1H, —CH—OH), 5.07(m, 1H, —CH-Ph$_2$), 2.75-2.78(m, 2H, CH$_2$), 2.50-3.50(m, 8H, piperazine).

EXAMPLE 3

VII-3 $N^1$-p-chlorobenzyl-$N^4$-[2-hydroxy-2-(benzo[b]thiophene-3-yl)]ethylpiperazine hydrochloride 5.0 g of $N^1$-(p-chlorobenzyl-$N^4$-[2-carbonyl-2-(benzo[b]thiophene-3-yl)]ethylpiperazine hydrochloride (13 mmol) was synthesized using $N^1$-p-chlorobenzylpiperazine (20 mmol) and 3-(2-chloracetyl)-benzo[b]thiophene (20 mmol) according to general method 4, then the reduction of carbonyl was performed according to general method 5. 4.6 g of product was obtained. m.p=250.1-252.3° C.(dec).

MS(m/z): 388.12[M+1]$^+$.

$^1$HNMR(DMSO): 7.78-7.87(m, 4H, Ar—H), 7.28-7.45(m, 4H, Ar—H), 7.22(s, 1H, thiophene), 4.60(d, J=10 Hz, 1H, —CH—OH), 5.07(m, 2H, —CH$_2$-Ph), 2.75-2.78(m, 2H, CH$_2$), 2.50-3.50(m, 8H, piperazine).

EXAMPLE 4

VII-4 $N^1$-benzyl-$N^4$-[1-methyl-2-hydroxy-2-(benzo[b]thiophene-3-yl)]ethylpiperazine (threo isomer)

4.37 g of $N^1$-phenyl-$N^4$-[1-methyl-2-carbonyl-2-(benzo[b]thiophene-3-yl)]ethylpiperazine hydrochloride (10 mmol) was synthesized using $N^1$-benzylpiperazine (20 mmol) and 3-(2-bromopropionyl)-benzo[b]thiophene(20 mmol) according to general method 4, then the reduction of carbonyl was performed according to general method 5. 1.2 g of product was obtained by separation via column chromatography. m.p=268.0-270.4° C.(dec).

MS(m/z): 367.2[M+1]$^+$.

$^1$HNMR(DMSO): 7.28-7.81(m, 5H, Ar—H), 7.24-7.28(m, 4H, Ar—H), 7.22(s, 1H, thiophene), 4.60(m, J=10 Hz, 1H, —CH—OH), 3.54(m, 2H, —CH$_2$-Ph), 2.75-2.78(m, 1H, —CH—CH$_3$), 2.52-2.74(m, 8H, piperazine), 0.93(d, 3H, CH—CH$_3$).

EXAMPLE 5

VII-5 N$^1$-benzyl-N$^4$-[1-methyl-2-hydroxy-2-(benzo[b]thiophene-3-yl)]ethylpiperazine (erythro isomer)

4.37 g of N$^1$-phenyl-N$^4$-[1-methyl-2-carbonyl-2-(benzo[b]thiophene-3-yl)]ethylpiperazine hydrochloride (10 mmol) was synthesized using N$^1$-benzyl piperazine (20 mmol) and 3-(2-bromopropionyl)-benzo[b]thiophene(20 mmol) according to general method 4, then the reduction of carbonyl was performed according to general method 5. 1.95 g of product was obtained by separation via column chromatography, m.p=220.7-222.0° C.(dec).

MS(m/z): 367.1[M+1]$^+$.

$^1$HNMR(DMSO): 7.28-7.79(m, 5H, Ar—H), 7.24-7.28(m, 4H, Ar—H), 7.17(s, 1H, thiophene), 5.14(m, 1H, —CH—OH), 3.53(m, 2H, —CH$_2$-Ph), 2.82-2.86(m, 1H, —CH—CH$_3$), 2.52-2.74(m, 8H, piperazine), 1.08(d, 3H, CH—CH$_3$).

EXAMPLE 6

VII-6 N$^1$-p-aminobenzyl-N$^4$-[1-methyl-2-hydroxy-2-(benzo[b]thiophene-3-yl)]ethylpiperazine hydrochloride 4.2 g of N$^1$-p-aminophenyl-N$^4$-[1-methyl-2-carbonyl-2-(benzo[b]thiophene-3-yl)]ethylpiperazine hydrochloride (11 mmol) was synthesized using N$^1$-p-aminobenzyl piperazine (20 mmol) and 3-(2-bromopropionyl)-benzo[b]thiophene(20 mmol) according to general method 4, then the reduction of carbonyl was performed according to general method 5. 3.2 g of product was obtained in a yield of 76.2%. m.p=255.7-257.4° C.(dec).

MS(m/z): 382.2[M+1]$^+$.

$^1$HNMR(DMSO): 7.28-7.81(m, 4H, Ar—H), 7.24-7.28(m, 4H, Ar—H), 7.22(s, 1H, thiophene), 4.60(m, J=10 Hz, 1H, —CH—OH), 4.0(m, 2H, NH$_2$), 3.54(m, 2H, —CH$_2$-Ph), 2.75-2.78(m, 1H, —CH—CH$_3$), 2.52-2.74(m, 8H, piperazine), 0.93(d, 3H, CH—CH$_3$).

EXAMPLE 7

VII-7 N$^1$-p-methoxybenzyl-N$^4$-[1-methyl-2-hydroxy-2-(benzo[b]thiophene-3-yl)]ethylpiperazine hydrochloride 5.1 g of N$^1$-(p-methoxy)benzyl-N$^4$-[1-methyl-2-carbonyl-2-(benzo[b]thiophene-3-yl)]ethylpiperazine hydrochloride (13 mmol) was synthesized using N$^1$-p-methoxy-benzylpiperazine (20 mmol) and 3-(2-bromopropionyl)-benzo[b]thiophene(20 mmol) according to general method 4, then the reduction of carbonyl was performed according to general method 5. 4.7 g of product was obtained. m.p=262.0-264.4° C.(dec).

MS(m/z): 397.1 [M+1]$^+$.

$^1$HNMR(DMSO): 7.28-7.81(m, 4H, Ar—H), 7.24-7.28(m, 4H, Ar—H), 7.22(s, 1H, thiophene), 4.60(m, J=10 Hz, 1H, —CH—OH), 3.54(m, 2H, —CH$_2$-Ph), 3.37(s, 3H$_2$O—CH$_3$), 2.75-2.78(m, 1H, —CH—CH$_3$), 2.52-2.74(m, 8H, piperazine), 0.93(d, 3H, CH—CH$_3$).

EXAMPLE 8

VII-8 N$^1$-p-ethoxybenzyl-N$^4$-[1-methyl-2-hydroxy-2-(benzo[b]thiophene-3-yl)]ethylpiperazine hydrochloride 4.37 g of N$^1$-p-ethoxybenzyl-N$^4$-[1-methyl-2-carbonyl-2-(benzo[b]thiophene-3-yl)]ethylpiperazine hydrochloride (10 mmol) was synthesized using N$^1$-p-ethoxy-benzyl piperazine (20 mmol) and 3-(2-bromopropionyl)-benzo[b]thiophene (20 mmol) according to general method 4, then the reduction of carbonyl was performed according to general method 5. 1.2 g of product was obtained in a yield of 27.3%. m.p=268.0-270.4° C.(dec).

MS(m/z): 411.2[M+1]$^+$.

$^1$HNMR(DMSO): 7.28-7.81(m, 4H, Ar—H), 7.24-7.28(m, 4H, Ar—H), 7.22(s, 1H, thiophene), 4.60(m, J=10 Hz, 1H, —CH—OH), 3.54(m, 2H, —CH$_2$-Ph), 3.37(m, 3H, O—CH$_3$), 2.75-2.78(m, 1H, —CH—CH$_3$), 2.52-2.74(m, 8H, piperazine), 2.49(m, 2H, CH$_2$CH$_3$), 1.24(m, 3H, CH$_2$CH$_3$), 0.93(d, 3H, CH—CH$_3$).

EXAMPLE 9

VII-9 N$^1$-p-hydroxybenzyl-N$^4$-[1-methyl-2-hydroxy-2-(benzo[b]thiophene-3-yl)]ethylpiperazine hydrochloride 4.2 g of N$^1$-p-hydroxybenzyl-N$^4$-[1-methyl-2-carbonyl-2-(benzo[b]thiophene-3-yl)]ethylpiperazine hydrochloride (11 mmol) was synthesized using N$^1$-p-hydroxybenzylpiperazine (20 mmol) and 3-(2-bromopropionyl)-benzo[b]thiophene (20 mmol) according to general method 4, then the reduction of carbonyl was performed according to general method 5. 3.7 g of product was obtained. m.p=256.4-258.3° C.(dec).

MS(m/z): 383.2[M+1]$^+$.

$^1$HNMR(DMSO): 7.28-7.81(m, 4H, Ar—H), 7.24-7.28(m, 4H, Ar—H), 7.22(s, 1H, thiophene), 4.60(m, J=10 Hz, 1H, —CH—OH), 3.54(m, 2H, —CH$_2$-Ph), 2.75-2.78(m, 1H, —CH—CH$_3$), 2.52-2.74(m, 8H, piperazine), 0.93(d, 3H, CH—CH$_3$).

EXAMPLE 10

VII-10 N$^1$-benzyl-N$^4$-[3-hydroxy-3-(benzo[b]thiophene-3-yl)]propylpiperazine hydrochloride 4.37 g of N$^1$-benzyl-N$^4$-[3-carbonyl-3-(benzo[b]thiophene-3-yl)]propylpiperazine hydrochloride (10 mmol) was synthesized using N$^1$-benzylpiperazine (20 mmol) and 3-(3-chlorpropionyl)-benzo[b]thiophene(20 mmol) according to general method 4, then the reduction of carbonyl was performed according to general method 5. 3.95 g of product was obtained in a yield of 90%. m.p=257.5-259.0° C.(dec).

MS(m/z): 367.1[M+1]$^+$.

$^1$HNMR(DMSO): 7.65-7.90(m,4H,Ar—H), 7.46(s,1H, thiophene), 7.43-7.45(m, 5H, Ar—H), 5.26-5.29 (m, 1H, CH$_2$CHOH), 4.28(s, 2H, N—CH$_2$-Ph), 3.51(m, 2H, —CHOH CH$_2$—), 2.58-3.51 (m,8H, piperazine), 2.24-2.56(m,2H,—CH$_2$CH$_2$N).

EXAMPLE 11

VII-11 $N^1$-cinnamyl-$N^4$-[3-hydroxy-3-(benzo[b]thiophene-3-yl)]propylpiperazine hydrochloride 4.63 g of $N^1$-cinnamyl-$N^4$-[3-carbonyl-3-(benzo[b]thiophene-3-yl)]propylpiperazine hydrochloride (10 mmol) was synthesized using $N^1$-cinnamylpiperazine(20 mmol)and 3-(3-chlorpropionyl))-benzo[b]thiophene(20 mmol) according to general method 4, then the reduction of carbonyl was performed according to general method 5. 4.35 g of product was obtained in a yield of 93%. m.p=191.5-192.4° C.(dec).

MS(m/z): 393.1[M+1]$^+$.

$^1$HNMR(DMSO): 7.65-7.90(m,4H,Ar—H),7.46(s,1H, thiophene), 7.43-7.45(m, 5H, Ar—H), 6.15-6.33(m, 2H, N—CH=CH-Ph), 5.26-5.29(m, 1H, CH$_2$CHOH), 3.73-3.74(m, 2H, N—CH$_2$—CH=),3.51(m, 2H, —CHOH CH$_2$—),2.58-3.51(m,8H, piperazine), 2.24-2.56 (m, 2H, =CH$_2$CH$_2$N).

EXAMPLE 12

VII-12 $N^1$-α-phenethyl-$N^4$-[3-hydroxy-3-(benzo[b]thiophene-3-yl)]propylpiperazine hydrochloride 4.50 g of $N^1$-α-phenethyl-$N^4$-[3-carbonyl-3-(benzo[b]thiophene-3-yl)]propyl piperazine hydrochloride (10 mmol) was synthesized using $N^1$-α-phenethylpiperazine (20 mmol) and 3-(3-chlorpropionyl))-benzo[b]thiophene(20 mmol) according to general method 4, then the reduction of carbonyl was performed according to general method 5. 3.0 g of product was obtained in a yield of 76.7%. m.p=189.1-192.2° C.(dec).

MS(m/z): 381.1[M+1]$^+$.

$^1$HNMR(DMSO): 7.65-7.94(m,4H,Ar—H),7.43-7.48(m, 5H,Ar—H), 5.21(m, 1H, CH—CH$_3$), 4.36-4.37(m, 1H, CH—OH), 3.50-3.60(m, —CH$_2$—CH$_2$—N), 3.20-3.50(m, 8H, piperazine), 2.56-2.58 (m, 2H, =CH$_2$—CH$_2$—N), 1.83 (d, 3H, CH—CH$_3$).

EXAMPLE 13

VII-13 $N^1$-p-methoxylbenzyl-$N^4$-[3-hydroxy-3-(benzo[b]thiophene-3-yl)]propyl piperazine hydrochloride 4.92 g of $N^1$-p-methoxylbenzyl-$N^4$-[3-carbonyl-3-(benzo[b]thiophene-3-yl)]propyl piperazine hydrochloride (10 mmol) was synthesized using $N^1$-p-methoxylbenzyl piperazine (20 mmol) and 3-(3-chlorpropionyl)-benzo[b]thiophene (20 mmol) according to general method 4, then the reduction of carbonyl was performed according to general method 5. 4.30 g of product was obtained in a yield of 87.4%. m.p=240.0-242.0° C. (dec).

MS(m/z): 420.9[M+1]$^+$.

$^1$HNMR(DMSO): 7.29-7.92(d, 4H, Ar—H), 7.47(s, 1H, thiophene), 7.00-7.21(m, 4H, Ar—H), 5.30-5.80(1H, —CH OH), 5.15(d, 1H, CH—OH), 3.73 (O—CH$_3$), 3.59(m, 2H, =CH$_2$—CH$_2$—N), 3.22-3.37(m, 8H, piperazine), 2.30-2.43 (m, 2H, CHOH—CH$_2$).

EXAMPLE 14

VII-14 $N^1$-benzhydryl-$N^4$-[3-hydroxy-3-(benzo[b]thiophene-3-yl)]propylpiperazine hydrochloride 5.13 g of $N^1$-benzhydryl-$N^4$-[3-carbonyl-3-(benzo[b]thiophene-3-yl)]propyl piperazine hydrochloride (10 mmol) was synthesized using $N^1$-benzhydryl piperazine(20 mmol) and 3-(3-chlorpropionyl)-benzo[b]thiophene (20 mmol) according to general method 4, then the reduction of carbonyl was performed according to general method 5. 2.95 g of product was obtained in a yield of 57.5%. m.p=119.2-121.0° C.(dec).

MS(m/z): 443.1[M+1]$^+$.

$^1$HNMR(DMSO):7.78-7.87(m, 6H, Ar—H), 7.28-7.45(m, 9H, Ar—H), 5.36-5.40(m, 1H, CH$_2$CHOH), 5.07(s, 1H, —CH-Ph$_2$),4.28-4.29(m, 2H, —CH$_2$—CH$_2$—N—), 2.50-3.50 (m, 8H, piperazine), 2.34(m, 2H, —CHOH—CH$_2$—).

EXAMPLE 15

VII-15 $N^1$-(4,4'-difluorodiphenylmethoxy))ethyl-$N^4$-[3-hydroxy-3-(benzo[b]thiophene-3-yl)]propylpiperazine hydrochloride 5.93 g of $N^1$-(4,4'-difluorodiphenylmethoxy)ethyl-$N^4$-[3-carbonyl-3-(benzo[b]thiophene-3-yl)]propylpiperazine hydrochloride (10 mmol) was synthesized using $N^1$-(4,4'-difluorodiphenylmethoxy)ethylpiperazine (20 mmol) and 3-(3-chlorpropionyl)-benzo[b]thiophene (20 mmol) according to general method 4, then the reduction of carbonyl was performed according to general method 5. 4.93 g of product was obtained in a yield of 82.8%. m.p=155.3-158.0° C.(dec).

MS(m/z): 523.1[M+1]$^+$.

$^1$HNMR(DMSO): 7.84-7.92(m, 4H, Ar—H), 7.48(s, 1H, thiophene), 7.32-7.39(m, 8H, Ar—H), 5.49(m, 1H, O—CH-Ph$_2$), 5.25(d, 1H, CH—OH), 3.76(m, 2H, —CH$_2$—CH$_2$—O), 3.27(m, 8H, piperazine), 3.12(br, 2H, —CH$_2$—CH$_2$—N), 2.80(br, 2H, N—CH$_2$—CH$_2$—), 2.36-2.40(m, 2H, CHOH—CH$_2$—).

EXAMPLE 16

VII-16 $N^1$-benzyl-$N^4$-[2-methyl-3-hydroxy-3-(benzo[b]thiophene-3-yl)]propyl piperazine hydrochloride 4.9 g of $N^1$-benzyl-$N^4$-[2-methyl-3-carbonyl-3-(benzo[b]thiophene-3-yl)]propyl piperazine hydrochloride (13 mmol) was synthesized using $N^1$-benzylpiperazine (20 mmol) and 3-(2-methyl-3-chlorpropionyl)-benzo[b]thiophene (20 mmol) according to general method 4, then the reduction of carbonyl was performed according to general method 5. 4.2 g of product was obtained. m.p=155.3-158.0° C.(dec).

MS(m/z): 381.1[M+1]$^+$.

$^1$HNMR(DMSO): 7.65-7.90(m,4H,Ar—H),7.46(s,1H, thiophene), 7.43-7.45(m, 5H, Ar—H), 5.26-5.29(m, 1H, —CHOH), 4.28(s, 2H, N—CH$_2$-Ph), 3.51(m, 1H, —CHOH CH—), 2.58-3.51 (m, 8H, piperazine),2.24-2.56(m,2H,—CHCH$_2$N),0.93 (d,3H,CH—CH$_3$).

EXAMPLE 17

VII-17 $N^1$-cinnamyl-$N^4$-[2-methyl-3-hydroxy-3-(benzo[b]thiophene-3-yl)]propyl piperazine hydrochloride 4.8 g of $N^1$-cinnamyl-$N^4$-[2-methyl-3-carbonyl-3-(benzo[b]thiophene-3-yl)]propyl piperazine hydrochloride (12 mmol) was synthesized using $N^1$-cinnamyl piperazine (16.2 mmol) and 3-(2-methyl-3-chlorpropionyl)-benzo[b]thiophene (20 mmol) according to general method 4, then the reduction of carbonyl was performed in general method 5. 4.3 g of product was obtained. m.p=157.2-158.9° C.(dec).

MS(m/z): 407.1[M+1]$^+$.

$^1$HNMR(DMSO): 7.65-7.90(m,4H,Ar—H),7.46(s,1H, thiophene),7.43-7.45(m, 5H, Ar—H),6.15-6.33(m, 2H, N—CHCH-Ph),5.26-5.29(m, 1H, —CHOH), 3.73-3.74(m, 2H, N—C$\underline{H_2}$—CH=), 3.51(m, 1H, —C$\underline{H}$OHCH—), 2.58-3.51 (m, 8$\underline{H}$, piperazine), 2.24-2.56 (m, 2H, —CHC$\underline{H_2}$N), 0.93(d, 3H, CH—C$\underline{H_3}$).

EXAMPLE 18

VII-18 N$^1$-benzhydryl-N$^4$-[2-methyl-3-hydroxy-3-(benzo[b]thiophene-3-yl)]propyl piperazine hydrochloride 4.5 g of N$^1$-benzhydryl-N$^4$-[2-methyl-3-carbonyl-3-(benzo[b]thiophene-3-yl)]propyl piperazine hydrochloride (10 mmol) was synthesized using N$^1$-benzhydrylpiperazine (16.2 mmol) and 3-(2-methyl-3-chlorpropionyl)-benzo[b]thiophene (20 mmol) according to general method 4, then the reduction of carbonyl was performed according to general method 5. 3.9 g of product was obtained in a yield of 86.6%. m.p=159.3-161.0° C.(dec).

MS(m/z): 457.1[M+1]$^+$.

$^1$HNMR(DMSO):7.65-7.90(m,4H,Ar—H),7.46(s,1H, thiophene),7.43-7.45(m, 10H, Ar—H), 5.26-5.29(m, 1H, —CHOH), 4.28(s, 1H, N—CH-Ph$_2$), 3.51(m, 1H, —CHOH C$\underline{H}$—), 2.58-3.51 (m,8H,piperazine), 2.24-2.56 (m,2H,—CH C$\underline{H_2}$N),0.93(d,3CH—C$\underline{H_3}$).

EXAMPLE 19

VII-19 N$^1$-(4,4'-difluorodiphenylmethoxy)ethyl-N$^4$-[2-methyl-3-hydroxy-3-(benzo[b]thiophene-3-yl)]propylpiperazine hydrochloride 5.9 g of N$^1$-(4,4'-difluorodiphenylmethoxy)ethyl-N$^4$-[2-methyl-3-carbonyl-3-(benzo[b]thiophene-3-yl)]propylpiperazine hydrochloride (11 mmol) was synthesized using N$^1$-(4,4'-difluorodiphenylmethoxy)ethylpiperazine(16.2 mmol) and 3-(2-methyl-3-chlorpropionyl)-benzo[b]thiophene(20 mmol) according to general method 4, then the reduction of carbonyl was performed according to general method 5. 4.8 g of product was obtained in a yield of 81.4%. m.p=154.3-155.0° C.(dec).

MS(m/z): 537.1[M+1]$^+$.

$^1$HNMR(DMSO): 7.84-7.92(m, 4H, Ar—H), 7.48(s, 1H, thiophene), 7.32-7.39(m, 8H, Ar—H), 5.49(m, 1H, O—CH-Ph$_2$), 5.25(d, 1H, CH—OH), 3.76(m, 2H, —CH$_2$—C$\underline{H_2}$—O), 3.27(m, 8H, piperazine), 3.12(m, 2H, —CH—C$\underline{H_2}$—N), 2.80(m, 2H, N—CH$_2$—CH$_2$—), 2.36-2.40(m, 1H, C$\underline{H}$OH—CH—),0.93(d,3H,C$\underline{H}$—CH$_3$).

EXAMPLE 20

VII-20 N$^1$-benzyl-N$^4$-[2-butyl-3-hydroxy-3-(benzo[b]thiophene-3-yl)]propyl piperazine hydrochloride 5.5 g of N$^1$-benzyl-N$^4$-[2-butyl-3-carbonyl-3-(benzo[b]thiophene-3-yl)]propyl piperazine hydrochloride (13 mmol) was synthesized using N$^1$-benzylpiperazine (16.2 mmol) and 3-(2-butyl-3-chlorpropionyl)-benzo[b]thiophene(20 mmol) according to general method 4, then the reduction of carbonyl was performed according to general method 5. 4.9 g of product was obtained in a yield of 89.1%. m.p=156.3-158.0° C.(dec).

MS(m/z): 423.1[M+1]$^+$.

$^1$HNMR(DMSO): 7.65-7.90(m,4H,Ar—H), 7.46(s,1H, thiophene), 7.43-7.45(m, 5H,Ar—H), 5.26-5.29(m, 1H,—CHOH), 4.28(s, 2H,N—C$\underline{H_2}$-Ph), 3.51(m,1H,—CHOH C$\underline{H}$—), 2.58-3.51 (m, 8H, piperazine), 2.24-2.56(m, 2H, —CHC$\underline{H_2}$N), 1.25-1.29(m, 6H, C$\underline{H_2}$—C$\underline{H_2}$—C$\underline{H_2}$—CH$_3$), 0.96 (3H,CH$_2$CH$_2$—C$\underline{H_3}$).

EXAMPLE 21

VII-21 N$^1$-α-phenemyl-N$^4$-[2-methyl-3-hydroxy-3-(benzo[b]thiophene-3-yl)]propyl piperazine hydrochloride 5.6 g of N$^1$-phenethyl-N$^4$-[2-butyl-3-carbonyl-3-(benzo[b]thiophene-3-yl)]propyl piperazine hydrochloride (13 mmol) was synthesized using N$^1$-α-phenethyl piperazine (16.2 mmol) and 3-(2-butyl-3-chlorpropionyl)-benzo[b]thiophene(20 mmol) according to general method 4, then the reduction of carbonyl was performed according to general method 5. 4.9 g of product was obtained in a yield of 87.5%. m.p=165.3-168.0° C.(dec).

MS(m/z): 437.1 [M+1]$^+$.

$^1$HNMR(DMSO): 7.65-7.90 (m,4H,Ar—H), 7.46(s ,1H, thiophene), 7.43-7.45(m, 5H,Ar—H), 5.26-5.29(m,1H,—CHOH), 4.28 (d,1H,N—CH-Ph), 3.51(m, 1H,—CHOH C$\underline{H}$—), 2.58-3.51 (m, 8H, piperazine), 2.24-2.56(m, 2H, —CHC$\underline{H_2}$N), 1.25-1.29(m, 6H, C$\underline{H_2}$—C$\underline{H_2}$—C$\underline{H_2}$—CH$_3$), 0.96(3H,CH$_2$CH$_2$—C$\underline{H_3}$), 1.34(m,3H,CHC$\underline{H_3}$).

EXAMPLE 22

VII-22 N$^1$-p-chlorobenzyl-N$^4$-[2-butyl-3-hydroxy-3-(benzo[b]thiophene-3 -yl)]propyl piperazine hydrochloride 5.5 g of N$^1$(p-chlorobenzyl)-N$^4$-[2-butyl-3-carbonyl-3-(benzo[b]thiophene-3-yl)]propylpiperazine hydrochloride (12 mmol) was synthesized using N$^1$-p-chlorobenzyl piperazine(16.2 mmol) and 3-(2-butyl-3-chlorpropionyl)-benzo[b]thiophene(20 mmol) according to general method 4, then the reduction of carbonyl was performed according to general method 5. 4.7 g of product is obtained in a yield of 85.4%. m.p=153.6-156.0° C.(dec).

MS(m/z): 458.1 [M+1]$^+$.

$^1$HNMR(DMSO):7.65-7.90(m,4H,Ar—H), 7.46(s,1H, thiophene), 7.43-7.45(m, 4H, Ar—H), 5.26-5.29(m, 1H,—CHOH), 4.28(s,2H,N—C$\underline{H_2}$-Ph), 3.51(m, 1H, —CHOH C$\underline{H}$—), 2.58-3.51 (m, 8H, piperazine), 2.24-2.56(m, 2H, —CHC$\underline{H_2}$N), 1.25-1.29(m, 6H, C$\underline{H_2}$—C$\underline{H_2}$—C$\underline{H_2}$—CH$_3$), 0.96(3H,CH$_2$CH$_2$—C$\underline{H_3}$).

EXAMPLE 23

VII-23 N$^1$-p-methoxylbenzyl-N$^4$-[2-butyl-3-hydroxy-3-(benzo[b]thiophene-3-yl)]propylpiperazine hydrochloride 5.9 g of N$^1$-p-methoxylbenzyl-N$^4$-[2-butyl-3-carbonyl-3-(benzo[b]thiophene-3-yl)]propylpiperazine hydrochloride (13 mmol) was synthesized using N$^1$-p-methoxyl benzylpiperazine(16.2 mmol) and 3-(2-butyl-3-chlorpropionyl)-benzo[b]thiophene (20 mmol) according to general method 4, then the reduction of carbonyl was performed according to general method 5. 5.2 g of product was obtained in a yield of 88.1%. m.p=159.7-162.0° C.(dec).

MS(m/z): 453.2[M+1]$^+$.

¹HNMR(DMSO):7.65-7.90(m,4H,Ar—H), 7.46(s,1H, thiophene), 7.43-7.45(m, 4H, Ar—H), 5.26-5.29(m, 1H,—CHOH), 4.28(s,2H,N—CH$_2$-Ph), 3.51(m, 1H, —CHOH CH$_2$—), 2.58-3.51 (m, 8H, piperazine), 2.24-2.56(m, 2H, —CHCH$_2$N), 1.25-1.29(m, 6H, CH$_2$—CH$_2$—CH$_2$—CH$_3$), 0.96(3H,CH$_2$CH$_2$—CH$_3$), 3.73(s,3H,—OCH$_3$).

EXAMPLE 24

VII-24 N$^1$-benzyl-N$^4$-[4-hydroxy-4-(benzo[b]thiophene-3-yl)]butylpiperazine hydrochloride 4.9 g of N$^1$-benzyl-N$^4$-[4-carbonyl-4-(benzo[b]thiophene-3-yl)]butylpiperazine hydrochloride (13 mmol) was synthesized using N$^1$-benzylpiperazine(16.2 mmol) and 3-(4-chlorbutyryl)-benzo[b]thiophene(20 mmol) according to general method 4, then the reduction of carbonyl was performed according to general method 5. 4.3 g of product was obtained in a yield of 87.8%. m.p=153.3-155.7° C.(dec).

MS(m/z): 381.1[M+1]$^+$.

¹HNMR(DMSO):7.65-7.90(d,4H,Ar—H), 7.46(s,1H, thiophene), 7.43-7.45(m, 5H, Ar—H), 5.26-5.29(m, 1H, CH$_2$CHOH), 4.28(s, 2H, N—CH2-Ph), 3.51(m, 2H, —CHOH CH$_2$—), 2.24-3.51 (m, 10H, piperazine), 1.28-1.32(m,4H, CH$_2$—CH$_2$—CH$_2$).

EXAMPLE 25

VII-25 N$^1$-α-phenethyl-N$^4$-[4-hydroxy-4-(benzo[b]thiophene-3-yl)]butylpiperazine hydrochloride 5.9 g of N$^1$-α-phenethyl-N$^4$-[4-carbonyl-4-(benzo[b]thiophene-3-yl)]butylpiperazine hydrochloride (15 mmol) was synthesized using N$^1$-α-phenethylpiperazine(16.2 mmol) and 3-(4-chlorobutyryl)-benzo[b]thiophene(20 mmol) according to general method 4, then the reduction of carbonyl was performed according to general method 5. 5.2 g of product was obtained in a yield of 88.1%. m.p=155.3-158.0° C.(dec).

MS(m/z): 395.1[M+1]$^+$.

¹HNMR(DMSO): 7.65-7.94(m,4H,Ar—H),7.73(s, 114, thiophene), 7.43-7.48(m, 5H, Ar—H),5.21(m, 1H, CH—CH$_3$, 4.36-4.37(m, 1H, CH—OH), 3.50-3.60(m, —CH$_2$—CH$_2$—N), 3.20-3.50 (m, 8H, piperazine), 2.56-2.58 (m, 2H, —CH$_2$—CH$_2$—N), 1.83(d, J=6.4, 3H, >CH—CH$_3$), 1.31(2H,CH—CH$_2$—CH$_2$).

EXAMPLE 26

VII-26 N$^1$-p-nitrobenzyl-N$^4$-[4-hydroxy-4-(benzo[b]thiophene-3-yl)]butylpiperazine hydrochloride 5.3 g of N$^1$-p-nitrobenzyl-N$^4$-[4-carbonyl-4-(benzo[b]thiophene-3-yl)]butylpiperazine hydrochloride (12 mmol) was synthesized using N$^1$-p-nitrobenzylpiperazine(16.2 mmol) and 3-(4-chlorobutyryl)-benzo[b]thiophene(20 mmol) according to general method 4, then the reduction of carbonyl was performed according to general method 5. 4.8 g of product was obtained. m.p=168.4-171.0° C.(dec).

MS(m/z): 442.1[M+1]$^+$.

¹HNMR(DMSO):7.65-7.90(d, 4H, Ar—H),7.46(s, 1H, thiophene),7.33-7.35(m, 4H, Ar—H), 5.26-5.29(m, 1H, CH$_2$CHOH), 4.28(s, 2H, N—CH$_2$-Ph), 3.51(m, 2H, —CHOH CH$_2$—), 2.24-3.51(m, 10H, piperazine), 1.28-1.32 (m,4H, CH$_2$—CH$_2$—CH$_2$).

EXAMPLE 27

VII-27 N$^1$-p-aminobenzyl-N$^4$-[4-hydroxy-4-(benzo[b]thiophene-3-yl)]butylpiperazine hydrochloride 5.5 g of N$^1$-p-aminobenzyl-N$^4$-[4-carbonyl-4-(benzo[b]thiophene-3-yl)]butylpiperazine hydrochloride (14 mmol) was synthesized using N$^1$-p-aminobenzylpiperazine (16.2 mmol) and 3-(4-chlorobutyryl)-benzo[b]thiophene(20 mmol) according to general method 4, then the reduction of carbonyl was performed according to general method 5. 4.7 g of product was obtained. m.p=158.0-161.1☐(dec).

MS(m/z): 396.1[M+1]$^+$.

¹HNMR(DMSO):7.65-7.90 (d, 4H, Ar—H),7.46(s, 1H, thiophene),7.48-7.5 5(m, 4H, Ar—H), 5.26-5.29(m, 1H, CH$_2$CHOH), 4.28(s, 2H, N—CH$_2$-Ph), 3.51(m, 2H, —CHOH CH$_2$—), 3.00(m, 2H, NH$_2$), 2.24-3.51(m, 10H, piperazine), 1.28-1.32(m, 4H, CH$_2$CH$_2$—CH$_2$).

EXAMPLE 28

VII-28 N$^1$-cinnamyl-N$^4$-[4-hydroxy-4-(benzo[b]thiophene-3-yl)]butylpiperazine hydrochloride 5.7 g of N$^1$-cinnamyl-N$^4$-[4-carbonyl-4-(benzo thiophene-3 -yl)]butylpiperazine hydrochloride (14 mmol) was synthesized using N$^1$-cinnamylpiperazine(16.2 mmol) and 3-(4-chlorobutyryl)-benzo[b]thiophene(20 mmol) according to general method 4, then the reduction of carbonyl was performed according to general method 5. 5.0 g of product was obtained in a yield of 87.8%. m.p=145.5-148.2☐(dec).

MS(m/z): 407.1 [M+1]$^+$.

¹HNMR(DMSO): 7.65-7.90(d,4H,Ar—H),7.46(s,1H, thiophene),7.43-7.45(m, 5H, Ar—H), 6.15-6.33(m,2H,—CH=CH-Ph),5.26-5.29(m, 1H, CH$_2$CHOH), 3.73-3.74(m, 2H, N—CH$_2$—CH=), 3.51(m, 2H, —CHOHCH$_2$—), 2.24-3.51(m, 10H, piperazine), 1.28-1.32 (m,4H,CH$_2$—CH$_2$—CH$_2$).

EXAMPLE 29

VII-29 N$^1$-benzhydryl-N$^4$-[4-hydroxy-4-(benzo[b]thiophene-3-yl)]butylpiperazine hydrochloride 5.5 g of N$^1$-benzhydryl-N$^4$-[4-carbonyl-4-(benzo[b]thiophene-3-yl)]butylpiperazine hydrochloride (12 mmol) was synthesized using N$^1$-benzhydrylpiperazine(16.2 mmol) and 3-(4-chlorobutyryl)-benzo[b]thiophene(20 mmol) according to general method 4, then the reduction of carbonyl was performed according to general method 5. 4.8 g of product was obtained in a yield of 87.3%. m.p=165.9-168.3☐(dec).

MS(m/z): 457.1[M+1]$^+$.

¹HNMR(DMSO): 7.78-7.87 (m, 4H, Ar—H), 7.46(s, 1H, thiophene), 7.28-7.45(m, 10H, Ar—H), 5.36-5.40(m, 1H, CH$_2$CHOH), 5.07(m, 1H, —CH-Ph$_2$), 4.28-4.29(m, 2H, —CH$_2$—CH$_2$—N—), 2.50-3.50(m, 8H, piperazine), 2.34(m, 2H, —CHOH—CH$_2$—), 1.30(2H,CH$_2$—CH$_2$—CH$_2$).

EXAMPLE 30

VII-30 N$^1$-(4,4-difluorodiphenylmethoxy)ethyl-N$^4$-[4-hydroxy-4-(benzo[b]thiophene-3-yl)]butylpiperazine hydrochloride 6.4 g of N'-(4,4-difluorodiphenylmethoxy)ethyl-N$^4$-[4-carbonyl-4-(benzo[b]thiophene-3-yl)]butylpiperazine hydrochloride (12 mmol) was synthesized using $N^1$-4,4'-difluorodiphenylmethoxy)ethylpiperazine (16.2 mmol) and 3-(4-chlorbutyryl)-benzo[b]thiophene(20 mmol) according to general method 4, then the reduction of carbonyl was performed according to general method 5. 5.3 g of product was obtained in a yield of 82.8%. m.p=157.3-159.7☐(dec).

MS(m/z): 537.1[M+1]$^+$.

$^1$HNMR(DMSO): 7.68-7.84(d,4H,Ar—H),7.48(s,1H, thiophene),7.32-7.39(m,8H, Ar—H), 5.49(m,1H,O—CH-Ph$_2$), 5.25(d,1H,CH—OH), 3.76(m, 2H, —CH$_2$—$\overline{CH_2}$—O), 3.27(m, 8$\overline{H}$, piperazine), 3.12(m, 2H, —CH$_2$—$\overline{CH_2}$—N), 2.80(m, 2H, N—$\underline{CH_2}$—CH$_2$—), 2.36-2.40(m, 2H, $\overline{CHOH}$—$\underline{CH_2}$—), 1.29(2H,$\overline{CH_2}$—$\underline{CH_2}$—CH$_2$).

EXAMPLE 31

VII-31 $N^1$-p-methoxylcinnamyl-$N^4$-[3-hydroxy-3-(benzo[b]thiophene-3-yl)]propyl piperazine hydrochloride 4.20 g of $N^1$-p-methoxylcinnamyl-$N^4$-[3-carbonyl-3-(benzo[b]thiophene-3-yl)]propyl piperazine hydrochloride (10 mmol) was synthesized using $N^1$-p-methoxylcinnamyl piperazine(20 mmol) and 3-(3-chloropropionyl)-benzo[b]thiophene (20 mmol) according to general method 4, then the reduction of carbonyl was performed according to general method 5. 3.87 g of product was obtained in a yield of 92%. m.p=256.5-258.0☐(dec).

MS(m/z): 367.1[M+1]$^+$.

$^1$HNMR(DMSO): 7.65-7.90 (m, 4H, Ar—H),7.46(s, 1H, thiophene),7.43-7.45(m, 4H, Ar—H), 6.32-6.39(m, 2H,—CH=CH—), 5.26-5.29(m, 1H, CH$_2$CHOH), 3.73-3.74(m, 2H, N—CH$_2$—CH=), 3.51(m, 2H, —$\overline{CHOH}$$\underline{CH_2}$—), 3.0(s, 1H, O$\underline{CH_3}$), 2.58-3.51(m, 8H, piperazine), 2.2$\overline{4}$-2.56 (m, 2H, —CH$_2$$\underline{CH_2}$N).

EXAMPLE 32

VII-32 $N^1$-p-aminocinnamyl-$N^4$-[3-hydroxy-3-(benzo[b]thiophene-3-yl)]propyl piperazine hydrochloride 4.03 g of $N^1$-p-aminocinnamyl-$N^4$-[3-carbonyl-3-(benzo[b]thiophene-3-yl)]propyl piperazine hydrochloride (10 mmol) was synthesized using $N^1$-p-aminocinnamyl piperazine(20 mmol) and 3-(3-chloropropionyl)-benzo[b]thiophene (20 mmol) according to general method 4, then the reduction of carbonyl was performed according to general method 5. 3.60 g of product was obtained in a yield of 88%. m.p=252.5-255.0☐(dec).

MS(m/z): 408.1[M+1]$^+$.

$^1$HNMR(DMSO): 7.65-7.90(m,4H,Ar—H),7.46(s,1H, thiophene),7.43 -7.45(m,4H, Ar—H), 6.32-6.39(m, 2H,—CH=CH—), 5.26-5.29(m, 1 H, CH$_2$CHOH), 4.0(s,2H, NH$_2$), 3.73-3.74 (m,2H,N—CH$_2$—CH=), 3.51(m,2H,—CHOHCH$_2$—), 2.58-3.51(m,8H,piperazine), 2.24-2.56 (m,2H,—CH$_2$CH$_2$N).

EXAMPLE 33

VII-33 $N^1$-(4,4'-difluorodiphenylmethoxy)ethyl-$N^4$-[3-hydroxy-3-(benzo[b]thiophene-3-yl)]propylpiperazine hydrochloride 5.01 g of $N^1$-(4,4'-difluorodiphenylmethoxy)ethyl-$N^4$-[3-carbonyl-3 -(benzo[b]thiophene-3-yl)]propylpiperazine hydrochloride (9 mmol) was synthesized using $N^1$-(4,4'-difluorodiphenylmethoxy)ethylpiperazine (20 mmol) and 3-(3-chloropropionyl)-benzo[b]thiophene(20 mmol) according to general method 4, then the reduction of carbonyl was performed according to general method 5. 4.15 g of product was obtained in a yield of 83%. m.p=267.5-269.0☐(dec).

MS(m/z): 556.1[M+1]$^+$.

$^1$HNMR(DMSO): 7.84-7.92(m, 4H, Ar—H), 7.48(s, 1H, thiophene), 7.32-7.39(m, 8H, Ar—H),5.49(s, 1H, O—CH-Ph$_2$), 5.25(d, 1H, CH—OH), 3.76(m, 2H, —CH$_2$—$\overline{CH_2}$—O). 3.27(m, 8H, piperazine), 3.12(m, 2H, —CH$_2$—$\overline{CH_2}$—N), 2.80(br, 2H, N—$\underline{CH_2}$—CH$_2$—), 2.36-2.40(m, 2H, $\overline{CHOH}$—$\underline{CH_2}$—).

EXAMPLE 34

VII-34 $N^1$-(4,4'-dihydroxydiphenylmethoxy)ethyl-$N^4$-[3-hydroxy-3-(benzo[b]thiophene-3-yl)]propylpiperazine hydrochloride 4.17 g of $N^1$-(4,4-dihydroxydiphenylmethoxy)ethyl-$N^4$-[3-carbonyl-3-(benzo[b]thiophene-3-yl)]propylpiperazine hydrochloride (8 mmol) was synthesized using $N^1$-(4,4'-dihydroxydiphenylmethoxy)ethylpiperazine (20 mmol) and 3-(3-chloropropionyl)-benzo[b]thiophene(20 mmol) according to general method 4, then the reduction of carbonyl was performed according to general method 5. 3.45 g of product was obtained in a yield of 83%. m.p=275.5-277.0☐(dec).

MS(m/z): 519.1[M+1]$^+$.

$^1$HNMR(DMSO): 7.84-7.92(m, 4H, Ar—H), 7.48(s, 1H, thiophene), 7.36-7.45(m, 8H, Ar—H), 5.49(s, 1H, O—CHPh$_2$), 5.25(d, 1H, CH—OH), 3.76(m, 2H, —CH$_2$—$\overline{CH_2}$—O), 3.27(m, 8H, piperazine), 3.12(m, 2H, —CH$_2$—$\overline{CH_2}$—N), 2.80(br, 2H, N—$\underline{CH_2}$—CH$_2$—), 2.36-2.40(m, 2H, $\overline{CHOH}$—$\underline{CH_2}$—).

EXAMPLE 35

VII-35 $N^1$-p-nitrocinnamyl-$N^4$-[3-hydroxy-3-(benzo[b]thiophene-3-yl)]propyl piperazine hydrochloride 3.90 g of $N^1$-p-nitrocinnamyl-$N^4$-[3-carbonyl-3-(benzo[b]thiophene-3-yl)]propyl piperazine hydrochloride (9 mmol) was synthesized using $N^1$-p-nitrocinnamyl piperazine (20 mmol) and 3-(3-chloropropionyl)-benzo[b]thiophene (20 mmol) according to general method 4, then the reduction of carbonyl was performed according to general method 5. 3.42 g of product was obtained in a yield of 87%. m.p=240.5-242.0☐(dec).

MS(m/z): 438.1[M+1]$^+$.

$^1$HNMR(DMSO): 7.65-7.90(m, 4H, Ar—H), 7.46(s, 111, thiophene), 7.43-7.45(m, 4H, Ar—H), 6.32-6.39(m, 2H, —CH=CH—), 5.26-5.29(m, 1H, CH$_2$CHOH), 3.73-3.74 (m, 2H, N—CH$_2$—CH=), 3.51(m, 2H, —CHOHCH$_2$—), 2.58-3.51(m, 8H, piperazine), 2.24-2.56(m, 2H, —CH$_2$CH$_2$N).

EXAMPLE 36

VII-36 $N^1$-benzyl-$N^4$-[3-hydroxy-3-(5-methylbenzo[b]thiophene-3-yl)]propyl piperazine hydrochloride 3.03 g of $N^1$-benzyl-$N^4$-[3-carbonyl-3-(5-methylbenzo[b]thiophene-3-yl)]propyl piperazine hydrochloride (8 mmol) was synthesized using $N^1$-benzylpiperazine (20 mmol) and 3-(3-chloropropionyl)-5-methylbenzo[b]thiophene(20 mmol) according to general method 4, then the reduction of carbonyl was performed according to general method 5. 2.65 g of product was obtained in a yield of 87%. m.p=252.5-254.0 (dec).

MS(m/z): 381.1[M+1]$^+$.

$^1$HNMR(DMSO): 7.65-7.90(m, 3H, Ar—H), 7.46(s, 1H, thiophene), 7.43-7.45(m, 5H, Ar—H), 5.26-5.29(m, 1H, CH$_2$CHOH), 4.28(s, 2H, N—CH$_2$-Ph), 3.51(m, 2H, —CHOH CH$_2$—), 2.35(m, 3H, CH$_3$), 2.58-3.51(m, 8H, piperazine), 2.24-2.56(m, 2H, —CH$_2$CH$_2$N).

EXAMPLE 37

VII-37 N$^1$-benzyl-N$^4$-[3-hydroxy-3-(5-methoxyl-benzo[b]thiophene-3-yl)]propyl piperazine hydrochloride 3.87 g of N$^1$-benzyl-N$^4$-[3-carbonyl-3-(5-methoxylbenzo[b]thiophene-3-yl)]propyl piperazine hydrochloride (10 mmol) was synthesized using N$^1$-benzylpiperazine (20 mmol) and 3-(3-chloropropionyl)-5-methoxylbenzo[b]thiophene (20 mmol) according to general method 4, then the reduction of carbonyl was performed according to general method 5. 3.35 g of product was obtained in a yield of 86%. m.p=252.5-255.0 (dec).

MS(m/z): 397.1[M+1]$^+$.

$^1$HNMR(DMSO): 7.65-7.90(m,3H,Ar—H),7.46(s,1H, thiophene),7.43-7.45 (m, 5H, Ar—H), 5.26-5.29(m, 1H, CH$_2$CHOH), 4.35(m,3H,—OCH$_3$), 4.28(s, 2H, N—CH$_2$-Ph), 3.51(m, 2H, —CHOHCH$_2$—), 2.58-3.51(m,8H,piperazine), 2.24-2.56(m,2H,—CH$_2$CH$_w$N).

EXAMPLE 38

VII-38 N$^1$-benzyl-N$^4$-[3-hydroxy-3-(6-aminobenzo[b]thiophene-3-yl)]propyl piperazine hydrochloride 3.42 g of N$^1$-benzyl-N$^4$-[3-carbonyl-3-(6-aminobenzo[b]thiophene-3-yl)]propyl piperazine hydrochloride (9 mmol) was synthesized using N$^1$-benzyl piperazine(20 mmol) and 3-(3-chloropropionyl)-6-aminobenzo[b]thiophene (20 mmol) according to general method 4, then the reduction of carbonyl was performed according to general method 5. 3.02 g of product was obtained in a yield of 88%. m.p=242.5-245.0 (dec).

MS(m/z): 382.1[M+1]$^+$.

$^1$HNMR(DMSO): 7.65-7.90(m, 3H, Ar—H),7.46(s, 1H, thiophene),7.43-7.45(m, 5H, Ar—H), 5.26-5.29(m, 1H, CH$_2$CHOH), 4.28(s, 2H, N—CH$_2$-Ph), 4.02(m,2H,—NH$_2$), 3.51 (m, 2H, —CHOHCH$_2$—), 2.58-3.51(m, 8H, piperazine), 2.24-2.56(m, 2H, —CH$_2$CH$_2$N).

EXAMPLE 39

VII-39 N$^1$-benzyl-N$^4$-[3-hydroxy-3-(6-chlorobenzo[b]thiophene-3-yl)]propyl piperazine hydrochloride 3.21 g of N$^1$-benzyl-N$^4$-[3-carbonyl-3-(6-chlorobenzo[b]thiophene-3-yl)]propyl piperazine hydrochloride (8 mmol) was synthesized using N$^1$-benzyl piperazine(20 mmol) and 3-(3-chloropropionyl)-6-chlorobenzo[b]thiophene (20 mmol) according to general method 4, then the reduction of carbonyl was performed according to general method 5. 3.01 g of product was obtained in a yield of 93%. m.p=251.5-253.0 (dec).

MS(m/z): 402.1 [M+1]$^+$.

$^1$HNMR(DMSO): 7.69-7.95(m, 3H, Ar—H), 7.46(s, 1H, thiophene), 7.43-7.45(m, 5H, Ar—H), 5.26-5.29(m, 1H, CH$_2$CHOH), 4.28(s, 2H, N—CH$_2$-Ph), 3.51(m, 2H, —CHOH CH$_2$—), 2.58-3.51(m,8H,piperazine),2.24-2.56(m,2H,—CH$_2$CH$_2$N).

EXAMPLE 40

VII-40 N$^1$-benzyl-N$^4$-[3-hydroxy-3-(6-methylaminobenzo[b]thiophene-3-yl)]propyl piperazine hydrochloride 3.87 g of N$^1$-benzyl-N$^4$-[3-carbonyl-3-(6-methylaminobenzo[b]thiophene-3-yl)]propyl piperazine hydrochloride (10 mmol) was synthesized using N$^1$-benzylpiperazine (20 mmol) and 3-(3-chloropropionyl)-6-methylaminobenzo[b]thiophene (20 mmol) according to general method 4, then the reduction of carbonyl was performed according to general method 5. 3.35 g of product was obtained in a yield of 86%. m.p=252.5-255.0 (dec).

MS(m/z): 396.1[M+1]$^+$.

$^1$HNMR(DMSO): 7.69-7.95 (m, 3H, Ar—H), 7.46(s, 1H, thiophene), 7.43-7.45(m, 5H, Ar—H), 5.26-5.29(m, 1H, CH$_2$CHOH), 4.28(s, 2H, N—CH$_2$-Ph), 4.0(m, 1H, NH), 3.51 (m, 2H, —CHOHCH$_2$—), 2.98-3.51(m, 8H, piperazine), 2.78(m, 3H, CH$_3$NH) 2.24-2.56 (m, 2H, —CH$_2$CH$_2$N).

EXAMPLE 41

VII-41 N$^1$-(β-pyridinemethyl)-N$^4$-[2-methyl-3-hydroxy-3-(benzo[b]thiophene-3yl)]propylpiperazine hydrochloride 4.9 g of N$^1$-(β-pyridinemethyl)-N$^4$-[2-methyl-3-carbonyl-3-(benzo[b]thiophene-3-yl)]propylpiperazine hydrochloride (13 mmol) was synthesized using N$^1$-(β-pyridinemethyl)piperazine (20 mmol) and 3-(2-methyl-3-chlorpropionyl)-benzo[b]thiophene (20 mmol) according to general method 4, then the reduction of carbonyl was performed according to general method 5. 4.2 g of product was obtained. m.p=157.3-159.0 (dec).

MS (m/z): 382.1[1\4+1]$^+$.

$^1$HNMR(DMSO): 7.65-7.90(m, 4H, Ar—H), 7.46(s, 1H, thiophene), 7.43-7.45(m, 4H, Ar—H), 5.26-5.29(m, 1H, —CHOH), 4.28(s, 2H, N—CH$_2$-Ph), 3.51(m, 1H, —CHOH CH—), 2.58-3.51 (m, 8H, piperazine), 2.24-2.56(m, 2H, —CHCH$_2$N), 0.93(d,3H,CH—CH$_3$).

EXAMPLE 42

VII-42 N$^1$-(4-morpholinebenzyl)-N$^4$-[2-methyl-3-hydroxy-3-(benzo[b]thiophene-3-yl)]propylpiperazine hydrochloride 5.2 g of N$^1$-(4-morpholinebenzyl)-N$^4$-[2-methyl-3-carbonyl-3-(benzo[b]thiophene-3-yl)]propylpiperazine hydrochloride (12 mmol) was synthesized using N$^1$-(4-morpholinebenzyl)piperazine (20 mmol) and 3-(2-methyl-3-chloropropionyl-benzo[b]thiophene (20 mmol) according to general method 4, then the reduction of carbonyl was performed according to general method 5. 4.5 g of product was obtained. m.p=151.3-153.0 (dec).

MS(m/z): 466.6[M+1]$^+$.

$^1$HNMR(DMSO): 7.65-7.90 (m, 4H, Ar—H), 7.46(s, 1H, thiophene), 7.43-7.45(m, 4H, Ar—H), 5.26-5.29(m, 1H, CH$_2$CHOH), 4.28(s, 2H, N—CH$_2$-Ph), 3.51(m, 1H,—CHOH CH—), 2.65-3.51(10H, piperazine, —CH$_2$—N, Comb),1.85-2.55(m, 8H, morphrine-H),1.06(d, 3H, CH$_3$).

EXAMPLE 43

VII-43 N$^1$-benzyl-N$^4$-[2-cyclopentylmethyl-3-hydroxy-3-(benzo[b]thiophene-3-yl)]propylpiperazine hydrochloride 5.2 g of N$^1$-benzyl-N$^4$-[2-cyclopentylmethyl-3-carbonyl-3-(benzo[b]thiophene-3-yl)]propylpiperazine hydrochloride (12 mmol) was synthesized using N$^1$-benzylpiperazine (20 mmol) and 3-(2-cyclopentylmethyl-3-chloropropionyl)-benzo[b]thiophene (20 mmol) according to general method 4, then the reduction of carbonyl was performed according to general method 5. 4.8 g of product was obtained. m.p=159.3-161.0☐(dec).

MS(m/z): 435.1[M+1]$^+$.

$^1$HNMR(DMSO):7.65-7.90(m,4H,Ar—H),7.46(s,1H, thiophene),7.43 -7.45 (m, 5H, Ar—H), 5.26-5.29 (m,1H,—CHOH), 4.28(s,2H,N—CH$_2$-Ph), 3.51(m,1H,—CHOH CH—), 2.58-3.51 (m,8H,piperazine), 2.24-2.56(m,2H,—CH CH$_2$N), 1.49-1.65(m,9H,Ar—H).

EXAMPLE 44

| Tablet: | derivatives of Example 1-43 | 10 mg |
|---|---|---|
| | sucrose | 150 mg |
| | corn starch | 38 mg |
| | calcium stearate | 2 mg |

Preparation: The active ingredient was mixed with sucrose and corn starch, then the mixture was wetted by adding water, stirred evenly, dried and then crushed and screened, then calcium stearate was added. The mixture obtained was stirred evenly and then pressed into tablets. The weight per tablet was 200 mg containing 10 mg of active ingredient.

EXAMPLE 45

| Injection: | derivatives of Example 1-43 | 20 mg |
|---|---|---|
| | water for injection | 80 mg |

Preparation: The active ingredient was mixed evenly with water for injection and filtered, then the mixture obtained was subpacked into ampoules under sterile conditions. The weight per ampoule was 10 mg containing 2 mg of active ingredient.

EXAMPLE 46

Pharmacological experimental studies on the in vivo and in vitro antidepression effect of the compounds.

1. Inhibition effect of the compounds on the uptake of 5-HT, NA and DA by brain synaptosomes Study on the reuptake of monoamine neurotransmitters by brain synaptosomes was performed, which is currently one of the important means adopted in the worldwide in pharmacological studies of central nervous. This method can not only be used to study the mechanism of drug's action, but also be used for screening new drugs acting by this mechanism. In this experiment, studies on the inhibition effect of the compounds of the present invention on the reuptake of 5-HT, NA and DA by brain synaptosomes was performed, using the method as mentioned above with Venlafaxine (an effective dual inhibitor on the reuptake of 5-HT and NA) and DOV 21947 (a triple inhibitor on the reuptake of 5-HT, NA and DA) as the positive controls. The method was as follows:

1.1 Preparation of rat brain synaptosomes

Male SD rats were sacrificed by cervical dislocation and then the brains thereof were taken out rapidly by decollation and placed on ice. Brain tissues related (for [$^3$H]5-HT and [$^3$H]NA reuptake experiment, prefrontal cortex was taken; for [$^3$H]DA reuptake experiment, corpus striatum was taken) were separated and weighed. 10 times (V/W) of 0.32 mol/L ice-cold sucrose solution was added and was homogenized electrically with glass-teflon. The homogenate was centrifugated at 4☐ at 1000 g×10 min. Then the supernatant was taken and centrifugated at 4☐ at 17000 g×20 min. The precipitation was suspended in 30 volume of KRH Buffer(125 mM NaCl, 4.8 mM KCl, 1.2 mM CaCl$_2$, 1.2 mM MgSO$_4$, 1.0 mM KH$_2$PO$_4$, 22 mM NaHCO$_3$, 25 mM HEPES, 10 mM Glucose, 10 mM Pargyline, 0.2 mg/ml Ascorbic Acid) and then was preserved in an ice bath for use. (for NA reuptake experiment, the cortex needed was suspended in 20 volume of KRH Buffer)

1.2 [$^3$H]5-HT/NA/DA reuptake experiments

According to the reference, stocked solution of the tested substance was thawed immediately before use and was diluted with KBH Buffer to 100 μmol/L. 50 μl thereof was added into 500 μl total reaction system, and the final concentration was 10 μmol/L. Then 50 μl suspended synaptic membrane was added and mixed evenly, incubated in water bath for 30 min at 37☐. Then 10 nmol/L [$^3$H] 5-HT (50 nmol/L [$^3$H]DA or 60 nmol/L [$^3$H]NA) was added. After incubated for 10 min, the reaction system was immediately taken out and the reaction was stopped by adding 2 ml of ice-cold 150 mmol/L Tris-HCl buffer solution. The samples were collected on the circular fiberglass membrane by vacuum filtration, and the membrane was washed 3 times with 3 ml of ice-cold Tris-HCl buffer solution. The membrane was removed, baked for 15 min in a far-infrared oven and placed into an EP tube. 1.5 ml scintillation fluid was added and was tested by liquid scintillation counter overnight. For the solvent control total connecting tube and the non-specific connecting tube, no tested substance was added; for the total connecting tube, 50 μl solvent was added; for the non-specific connecting tube in the [$^3$H]5-HT reuptake experiment, 600 μmol/L Cocaine was added; for the non-specific connecting tube in the [$^3$H]NA reuptake experiment, 100 μmol/L DOV 21947 was added; for the non-specific connecting tube in the [$^3$H]DA reuptake experiment, 600 μmol/L Cocaine was added.

1.3 Results: At the same concentration condition(the control drugs and the tested substances were all 0.1 mmol/L), with Venlafaxine (an antidepressant already saled in the market) and DOV 21947(a new compound at phase II clinical trial) being as positive controls, the results determined of the inhibition rates for the reuptake of 5-HT, NA and DA were shown in table 2.

TABLE 2

Inhibition effect of the compounds on the uptake of 5-HT, NA and DA by brain synaptosomes

| compounds | inhibition effect on the uptake of 5-HT | inhibition effect on the uptake of NA | inhibition effect on the uptake of DA |
|---|---|---|---|
| VII-4 | 40.2 ± 11.0*# | 60.1 ± 4.1 | 14.5 ± 10.0*# |
| VII-5 | 73.6 ± 8.7*# | 26.2 ± 5.2*# | 11.4 ± 11.5*# |
| VII-10 | 95.6 ± 2.5*# | 77.4 ± 13.8 | 78.0 ± 8.0*# |

TABLE 2-continued

Inhibition effect of the compounds on the uptake of 5-HT, NA and DA by brain synaptosomes

| compounds | inhibition effect on the uptake of 5-HT | inhibition effect on the uptake of NA | inhibition effect on the uptake of DA |
|---|---|---|---|
| VII-11 | 101.2 ± 1.3 | 49.7 ± 13.8 | 97.9 ± 1.1*# |
| VII-12 | 103.6 ± 0.5* | 50.8 ± 2.7 | 98.0 ± 1.5*# |
| VII-14 | 77.8 ± 5.8*# | 44.9 ± 17.6 | 87.3 ± 4.3*# |
| VII-15 | 101.6 ± 1.2 | 53.5 ± 8.6 | 102.2 ± 1.3* |
| Venlafaxine | 106.9 ± 1.7 | 46.4 ± 4.6 | 48.6 ± 4.1 |
| DOV 21947 | 108.6 ± 3.8 | 61.9 ± 6.0 | 104.1 ± 4.2* |

*compared with Venlafaxine, $p < 0.05$;
compared with DOV 21047, $p < 0.05$

At the concentration of 10 μmol/L, the five compounds, i.e., VII-10, VII-11, VII-12, VII-14 and VII-15 had stronger inhibition activity on the reuptake of 5-HT, NA and DA. They showed similar potency to those of Venlafaxine and DOV 21947.

2. Results of in vivo antidepression of compound VII-10

A preliminary study was carried out on the in vivo antidepression effect of compound VII-10 using the Forced Swimming Test in Learned Helplessness Experiment, with Venlafaxine as the positive control. The results were shown in table 3:

TABLE 3

Results of forced swimming test of preferred compounds

| compounds | dosage (mg/kg) | immobility time (s) |
|---|---|---|
| CMC-Na | 20 ml/kg | 138 ± 30.1 |
| Venlafaxine | 18.24 | 80.8 ± 46.8* |
|  | 9.12 | 77.4 ± 47.2** |
|  | 4.56 | 57.1 ± 37.8** |
| VII-10 | 25.4 | 84 ± 48.9** |
|  | 12.7 | 87.5 ± 35.7 |
|  | 6.35 | 90.7 ± 46.3 |

*compared with positive group, $p < 0.5$, significant difference exists;
**compared with positive group, $p < 0.05$, extremely significant difference exists.

In the forced swimming test, VII-10 was able to significantly reduce the immobility time in swimming due to despair in the water. The efficacy (84±48.9 s) at the dose of 25.4 mg/kg was similar to that of positive control Venlafaxine (80.8±46.8 s) at the same molar quantities, i.e., 18.24 mg/kg, which showed extremely significant difference from the blank group. It suggests that VII-10 had a much stronger in vivo antidepression activity and the potency was similar to Venlafaxine.

3. Acute toxicity

Initial screening was performed by the method reported in "Modern Pharmacological Experiments Mothods" edited by Zhang Juntian. The $LD_{50}$ for mice single-fed was 1.1 g/kg of compound VII-10, which was obtained via statistics of Bliss.

4. Bacterial reverse mutation test for VII-10.

Bacterium: histidine auxotrophic mutant strains of Salmonella $TA_{97}$, $TA_{98}$, $TA_{100}$ and $TA_{102}$ Experimental method: the method reported in the literature: Maron D M et al: (1983) Mutay Res. 113, 173-216.

Results: The experiment included two parts: $-S_9$ and $+S_9$. $TA_{98}$ in $-S_9$ test system and $TA_{97}$ in $+S_9$ test system both showed bacteriostatic effect at 5000 μg per culture dish. The other dosages had no bacteriostatic effect for all the strains, with a well growing background. For all the dosages tested, both in $-S_9$ and $+S_9$ test systems, no significant increase of number of reverse mutation colonies was found. Ames test result was negative.

What is claimed is:

1. A benzothiophene alkanol piperazine derivative, characterized in that said benzothiophene alkanol piperazine derivative is a compound of formula (1)

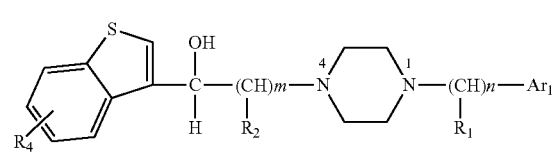

(1)

or a pharmaceutically acceptable salt thereof, optionally containing 0.5 to 3 molecules of crystal water,
wherein,
$Ar_1$ represents:

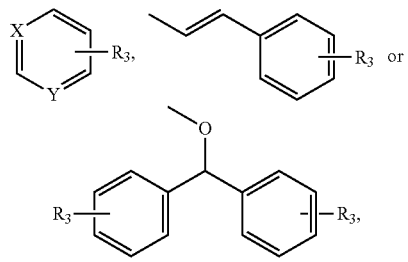

$R_1$ and $R_2$ each independently represent hydrogen; $C_1$-$C_6$ alkyl; $C_5$ or $C_6$ alicyclic ring; phenyl; or phenyl substituted by $C_1$-$C_6$ alkyl, $C_1$-$C_6$ alkoxy or halo groups;

$R_3$ and $R_4$ each independently represent hydrogen; $C_1$-$C_6$ alkyl; phenyl; or phenyl substituted by one to four substituents independently selected from the groups consisting of $C_1$-$C_6$ alkyl, hydroxyl, amino or halo; a 5-member or 6-member heterocyclic ring having a N and an O heteroatom as ring members; hydroxyl; $C_1$-$C_6$ alkoxy; amino; amino substituted by $C_1$-$C_6$ alkyl or $C_1$-$C_6$ haloalkyl; halo; carboxy, nitro or cyanomethyl;

X represents C or N;
Y represents C or N;
m is 1, 2 or 3, and
n is 1, 2 or 3.

2. The benzothiophene alkanol piperazine derivative according to claim 1, characterized in that, $R_3$ is hydrogen; $C_1$-$C_2$ alkyl; hydroxyl; methoxy; ethoxy; amino; amino substituted by $C_1$-$C_6$ alkyl or $C_1$-$C_6$ haloalkyl; fluorine atom; phenyl; or phenyl substituted by one to four substituents independently selected from the groups consisting of $C_1$-$C_6$ alkyl, $C_1$-$C_6$ alkoxy, hydroxyl, amino and halo.

3. The benzothiophene alkanol piperazine derivative according to claim 1, characterized in that, $R_3$ is $C_1$-$C_2$ alkyl or fluorine atom.

4. The benzothiophene alkanol piperazine derivative according to claim 1, characterized in that, the pharmaceutically acceptable salt is a hydrochloride salt, a hydrobromide salt, a sulphate salt, a trifluoroacetate salt or a methanesulfonate salt.

5. The benzothiophene alkanol piperazine derivative according to claim 1, characterized in that, it is selected from:

VII-1 $N^1$-benzyl-$N^4$-[2-hydroxy-2-(benzo[b]thiophene-3-yl)]ethylpiperazine,
VII-2 $N^1$-benzhydryl-$N^4$-[2-hydroxy-2-(benzo[b]thiophene-3-yl)]ethylpiperazine,
VII-3 $N^1$-(p-chlorobenzyl)-$N^4$-[2-hydroxy-2-(benzo[b]thiophene-3-yl)]ethylpiperazine,
VII-4 $N^1$-benzyl-$N^4$-[1-methyl-2-hydroxy-2-(benzo[b]thiophene-3-yl)]ethylpiperazine (threo isomer),
VII-5 $N^1$-benzyl-$N^4$-[1-methyl-2-hydroxy-2-(benzo[b]thiophene-3-yl)]ethylpiperazine (erythro isomer),
VII-6 $N^1$-p-aminobenzyl-$N^4$-[1-methyl-2-hydroxy-2-(benzo[b]thiophene-3-yl)]ethylpiperazine,
VII-7 $N^1$-p-methoxybenzyl-$N^4$-[1-methyl-2-hydroxy-2-(benzo[b]thiophene-3-yl)]ethylpiperazine,
VII-8 $N^1$-p-ethoxybenzyl-$N^4$-[1-methyl-2-hydroxy-2-(benzo[b]thiophene-3-yl)]ethylpiperazine,
VII-9 $N^1$-(p-hydroxybenzyl-$N^4$-[1-methyl-2-hydroxy-(benzo[b]thiophene-3-yl)]ethylpiperazine,
VII-10 $N^1$-benzyl-$N^4$-[3-hydroxy-3-(benzo[b]thiophene-3-yl)]propylpiperazine,
VII-11 $N^1$-cinnamyl-$N^4$-[3-hydroxy-3-(benzo[b]thiophene-3-yl)]propylpiperazine,
VII-12 $N^1$-α-phenethyl-$N^4$-[3-hydroxy-3-(benzo[b]thiophene-3-yl)]propylpiperazine,
VII-13 $N^1$-p-methoxybenzyl)-$N^4$-[3-hydroxy-3-(benzo[b]thiophene-3-yl)]propylpiperazine,
VII-14 $N^1$-benzhydryl-$N^4$-[3-hydroxy-3-(benzo[b]thiophene-3-yl)]propylpiperazine,
VII-15 $N^1$-(4,4'-difluorodiphenylmethoxyl)ethyl-$N^4$-[3-hydroxy-3-(benzo[b]thiophene-3-yl)]propylpiperazine,
VII-16 $N^4$-benzyl-$N^4$-[2-methyl-3-hydroxy-3-(benzo[b]thiophene-3-yl)]propylpiperazine,
VII-17 $N^4$-cinnamyl-$N^4$-[2-methyl-3-hydroxy-3-(benzo[b]thiophene-3-yl)]propylpiperazine,
VII-18 $N^1$-benzhydryl-$N^4$-[2-methyl-3-hydroxy-3-(benzo[b]thiophene-3-yl)]propylpiperazine,
VII-19 $N^1$-(4,4'-difluorodiphenylmethoxy)ethyl-$N^4$-[2-methyl-3-hydroxy-3-(benzo[b]thiophene-3-yl)]propylpiperazine,
VII-20 N-benzyl-$N^4$-[2-butyl-3-hydroxy-3-(benzo[b]thiophene-3-yl)]propylpiperazine,
VII-21 $N^1$-α-phenethyl-$N^4$-[2-butyl-3-hydroxy-3-(benzo[b]thiophene-3-yl)]propylpiperazine,
VII-22 $N^1$-(p-chlorobenzyl)-$N^4$-[2-butyl-3-hydroxy-3-(benzo[b]thiophene-3-yl)]propylpiperazine,
VII-23 $N^1$-(p-methoxybenzyl)-$N^4$-[2-butyl-3-hydroxy-3-(benzo[b]thiophene-3-yl)]propylpiperazine,
VII-24 $N^1$-benzyl-$N^4$-[4-hydroxy-4-(benzo[b]thiophene-3-yl)]butylpiperazine,
VII-25 $N^1$-α-phenethyl-$N^4$-[4-hydroxy-4-(benzo[b]thiophene-3-yl)]butylpiperazine,
VII-26 $N^1$-p-nitrobenzyl-N4-[4-hydroxy-4-(benzo[b]thiophene-3-yl)]butylpiperazine,
VII-27 $N^1$-p-aminobenzyl-$N^4$-[4-hydroxy-4-(benzo[b]thiophene-3-yl)]butylpiperazine,
VII-28 $N^1$-cinnamyl-$N^4$-[4-hydroxy-4-(benzo[b]thiophene-3-yl)]butylpiperazine,
VII-29 $N^1$-benzhydryl-$N^4$-[4-hydroxy-4-(benzo[b]thiophene-3-yl)]butylpiperazine,
VII-30 $N^1$-(4,4'-difluorodiphenylmethoxy)ethyl-$N^4$-[4-hydroxy-4-(benzo[b]thiophene-3-yl)]butylpiperazine,
VII-31 $N^1$-(p-methoxylcinnamyl)-$N^4$-[3-hydroxy-3-(benzo[b]thiophene-3-yl)]propylpiperazine,
VII-32 $N^1$-p-aminocinnamyl-$N^4$-[3-hydroxy-3-(benzo[b]thiophene-3-yl)]propylpiperazine,
VII-33 $N^1$-(4,4'-difluorodiphenylmethoxy)ethyl-$N^4$-[3-hydroxy-3-(benzo[b]thiophene-3-yl)]propylpiperazine,
VII-34 $N^1$-(4,4'-dihydroxydiphenylmethoxy)ethyl-$N^4$-[3-hydroxy-3-(benzo[b]thiophene-3-yl)]propylpiperazine,
VII-35 $N^1$-p-nitrocinnamyl-$N^4$-[3-hydroxy-3-(benzo[b]thiophene-3-yl)]propylpiperazine,
VII-36 $N^1$-benzyl-$N^4$-[3-hydroxy-3-(5-methylbenzo[b]thiophene-3-yl)]propylpiperazine,
VII-37 $N^1$-benzyl-$N^4$-[3-hydroxy-3-(5-methoxylbenzo[b]thiophene-3-yl)]propylpiperazine,
VII-38 $N^1$-benzyl-$N^4$-[3-hydroxy-3-(6-aminobenzo[b]thiophene-3-yl)]propylpiperazine,
VII-39 $N^1$-benzyl-$N^4$-[3-hydroxy-3-(6-chlorobenzo[b]thiophene-3-yl)]propylpiperazine,
VII-40 $N^1$-benzyl-$N^4$-[3-hydroxy-3-(6-methylaminobenzo[b]thiophene-3-yl)]propylpiperazine,
VII-41 $N^1$-(β-pyridinemethyl)-$N^4$-[2-methyl-3-hydroxy-3-(benzo[b]thiophene-3-yl)]propylpiperazine,
VII-42 $N^1$-(4-morpholinebenzyl)-$N^4$-[2-methyl-3-hydroxy-3-(benzo[b]thiophene- 3-yl)]propylpiperazine, and
VII-43 $N^1$-benzyl-$N^4$-[2-cyclopentylmethyl-3-hydroxy-3-(benzo[b]thiophene-3-yl)]propylpiperazine.

6. A pharmaceutical composition for antidepression, characterized in that, said pharmaceutical composition comprises therapeutically effective amount of benzothiophene alkanol piperazine derivative according to claim 1, together with a pharmaceutically acceptable carrier.

7. A method for treating depression, comprising administrating therapeutically effective amount of benzothiophene alkanol piperazine derivative according to claim 1 to a subject in need thereof.

\* \* \* \* \*

UNITED STATES PATENT AND TRADEMARK OFFICE
CERTIFICATE OF CORRECTION

PATENT NO.      : 8,680,097 B2                                  Page 1 of 1
APPLICATION NO. : 13/001998
DATED           : March 25, 2014
INVENTOR(S)     : Li et al.

It is certified that error appears in the above-identified patent and that said Letters Patent is hereby corrected as shown below:

Title page, in column 2, Item (56) under "Other Publications", line 8, delete "thiophen" and insert --thiophene--, therefor Title page, in column 2, Item (56) under "Other Publications", line 13, delete "αhydroxyl" and insert --α-hydroxyl--, therefor In the Claims In column 31, line 31, in Claim 5, delete "$N^4$" and insert --$N^1$--, therefor In column 31, line 33, in Claim 5, delete "$N^4$" and insert --$N^1$--, therefor In column 31, line 40, in Claim 5, delete "N" and insert --$N^1$--, therefor In column 32, line 3, in Claim 5, delete "N4" and insert --$N^4$--, therefor In column 32, line 36, in Claim 5, delete "(benzo[b]thiophene- 3-yl)" and insert --(benzo[b]thiophene-3-yl)--, therefor Signed and Sealed this
Eleventh Day of November, 2014

Michelle K. Lee
*Deputy Director of the United States Patent and Trademark Office*